United States Patent
Sun et al.

(10) Patent No.: US 9,664,644 B2
(45) Date of Patent: *May 30, 2017

(54) SYSTEM AND APPARATUS FOR DETERMINING TEMPERATURES IN A FLUID ANALYTE SYSTEM

(71) Applicant: Bayer HealthCare LLC, Whippany, NJ (US)

(72) Inventors: Steve Hoi-Cheong Sun, Mount Kisco, NY (US); Swetha Chinnayelka, Tarrytown, NY (US); John P. Creaven, Pearl River, NY (US); Andrew J. Edelbrock, Granger, IN (US); Matthew B. Holzer, Bronx, NY (US); Narasinha C. Parasnis, Nanuet, NY (US); Jeffery S. Reynolds, New Fairfield, CT (US); Paul M. Ripley, Nanuet, NY (US); Steven C. Charlton, Osceola, IN (US); Xin Wang, Mechanicville, NY (US); Mu Wu, Hopewell Junction, NY (US)

(73) Assignee: Ascensia Diabetes Care Holdings AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/749,318

(22) Filed: Jun. 24, 2015

(65) Prior Publication Data
US 2015/0293055 A1    Oct. 15, 2015

Related U.S. Application Data

(60) Division of application No. 14/094,434, filed on Dec. 2, 2013, now Pat. No. 9,097,650, which is a
(Continued)

(51) Int. Cl.
*G01N 27/327*    (2006.01)
*G01N 27/416*    (2006.01)
(Continued)

(52) U.S. Cl.
CPC ........... *G01N 27/4166* (2013.01); *A61B 5/01* (2013.01); *A61B 5/14546* (2013.01); *G01K 3/08* (2013.01);
(Continued)

(58) Field of Classification Search
CPC .................................... G01N 27/327–27/3274
See application file for complete search history.

(56) References Cited

U.S. PATENT DOCUMENTS

| 3,578,405 A | 5/1971 | Woodle ......................... 436/140 |
| 4,482,261 A | 11/1984 | Dewey et al. ................. 374/181 |

(Continued)

FOREIGN PATENT DOCUMENTS

| EP | 1087217 | 3/2001 |
| EP | 1141684 | 2/2005 |

(Continued)

OTHER PUBLICATIONS

The online Merriam-Webster definition of "thermocouple", downloaded on Jun. 21, 2016.*
(Continued)

*Primary Examiner* — Alexander Noguerola
(74) *Attorney, Agent, or Firm* — Nixon Peabody LLP

(57) ABSTRACT

A test sensor includes a body, a first conductive trace, a second conductive trace, and a third conductive trace. The body includes a first region that has a fluid-receiving area, a second region separate from the first region, and a first temperature sensing interface disposed at or adjacent to the fluid-receiving area. The fluid-receiving area receives a sample. The first trace is disposed on the body, and at least a portion of the first trace is disposed in the first region. The second and third traces are disposed on the body. The third trace extends from the first to the second regions. The third trace is connected to the first trace at the first temperature
(Continued)

sensing interface. The third trace includes a different material than the first trace. A first thermocouple is formed at the first temperature sensing interface. The thermocouple provides temperature data to determine an analyte concentration.

19 Claims, 11 Drawing Sheets

Related U.S. Application Data continuation of application No. 12/821,976, filed on Jun. 23, 2010, now Pat. No. 8,617,381.

(60) Provisional application No. 61/219,549, filed on Jun. 23, 2009.

(51) Int. Cl.

| | | |
|---|---|---|
| *A61B 5/01* | (2006.01) | |
| *G01K 3/08* | (2006.01) | |
| *G01K 7/01* | (2006.01) | |
| *G01K 7/02* | (2006.01) | |
| *G01K 7/16* | (2006.01) | |
| *G01K 13/00* | (2006.01) | |
| *G01N 27/26* | (2006.01) | |
| *G01N 27/30* | (2006.01) | |
| *A61B 5/145* | (2006.01) | |
| *A61B 5/1486* | (2006.01) | |

(52) U.S. Cl.
CPC ............ *G01K 7/01* (2013.01); *G01K 7/02* (2013.01); *G01K 7/16* (2013.01); *G01K 13/00* (2013.01); *G01N 27/26* (2013.01); *G01N 27/308* (2013.01); *G01N 27/3272* (2013.01); *G01N 27/3274* (2013.01); *A61B 5/1486* (2013.01); *A61B 5/14532* (2013.01); *Y10T 29/49155* (2015.01)

(56) References Cited

U.S. PATENT DOCUMENTS

| | | | |
|---|---|---|---|
| 4,718,777 A | 1/1988 | Mydynski et al. | 374/181 |
| 4,935,345 A | 6/1990 | Guilbeau et al. | 435/14 |
| 5,304,405 A | 4/1994 | Kobayashi et al. | 427/534 |
| 5,304,495 A | 4/1994 | Yim | 436/68 |
| 6,068,400 A | 5/2000 | Nelson et al. | 374/179 |
| 6,144,869 A | 11/2000 | Berner et al. | 600/347 |
| 6,233,471 B1 | 5/2001 | Berner et al. | 600/345 |
| 6,238,085 B1 | 5/2001 | Higashi et al. | 374/10 |
| 6,356,776 B1 | 3/2002 | Berner et al. | 600/347 |
| 6,594,514 B2 | 7/2003 | Berner et al. | 600/347 |
| 6,595,919 B2 | 7/2003 | Berner et al. | 600/365 |
| 6,645,368 B1 | 11/2003 | Beaty et al. | 205/792 |
| 6,780,296 B1 | 8/2004 | Bhullar et al. | 204/403.01 |
| 6,816,537 B2 | 11/2004 | Liess | 372/109 |
| 6,825,044 B2 | 11/2004 | Zheng et al. | 436/164 |
| 6,850,790 B2 | 2/2005 | Berner et al. | 600/347 |
| 6,866,758 B2 | 3/2005 | Bhullar et al. | 204/403.02 |
| 6,898,451 B2 | 5/2005 | Wuori | 600/322 |
| 7,174,199 B2 | 2/2007 | Berner et al. | |
| 7,295,867 B2 | 11/2007 | Berner et al. | 600/345 |
| 7,338,637 B2 | 3/2008 | Pease et al. | 422/68.1 |
| 7,338,639 B2 | 3/2008 | Burke et al. | 422/82.01 |
| 7,361,830 B2 | 4/2008 | Richetto et al. | 136/233 |
| 7,390,667 B2 | 6/2008 | Burke et al. | 436/95 |
| 7,407,811 B2 | 8/2008 | Burke et al. | 436/95 |
| 7,452,457 B2 | 11/2008 | Burke et al. | 205/792 |
| 7,460,958 B2 | 12/2008 | Walsh et al. | 702/24 |
| 7,480,032 B2 | 1/2009 | Braig et al. | 356/39 |
| 8,617,381 B2 * | 12/2013 | Sun | A61B 5/01 204/400 |
| 2002/0081231 A1 | 6/2002 | Shapiro et al. | 422/68.1 |
| 2003/0064525 A1 | 4/2003 | Liess | 436/149 |
| 2003/0153821 A1 | 8/2003 | Berner et al. | 600/345 |
| 2003/0160155 A1 | 8/2003 | Liess | 250/221 |
| 2003/0175806 A1 | 9/2003 | Rule et al. | 435/7.1 |
| 2004/0005716 A9 | 1/2004 | Beaty et al. | 436/149 |
| 2004/0132171 A1 | 7/2004 | Rule et al. | 435/287.2 |
| 2004/0157337 A1 | 8/2004 | Burke et al. | 436/70 |
| 2004/0157338 A1 | 8/2004 | Burke et al. | 436/147 |
| 2004/0157339 A1 | 8/2004 | Burke et al. | 436/149 |
| 2004/0167801 A1 | 8/2004 | Say et al. | 705/2 |
| 2004/0238357 A1 | 12/2004 | Bhullar et al. | 204/400 |
| 2004/0256248 A1 | 12/2004 | Burke et al. | 205/792 |
| 2004/0259180 A1 | 12/2004 | Burke et al. | 435/14 |
| 2005/0009101 A1 | 1/2005 | Blackburn | 435/7.1 |
| 2005/0070771 A1 | 3/2005 | Rule et al. | 600/316 |
| 2005/0148003 A1 | 7/2005 | Keith et al. | 435/6 |
| 2006/0004267 A1 | 1/2006 | Rule et al. | 600/310 |
| 2006/0020179 A1 | 1/2006 | Anderson et al. | 600/309 |
| 2006/0085137 A1 | 4/2006 | Bartkowiak et al. | 702/19 |
| 2006/0133960 A1 | 6/2006 | Ahmad | 422/83 |
| 2006/0156796 A1 | 7/2006 | Burke et al. | 73/61.44 |
| 2007/0038053 A1 | 2/2007 | Berner et al. | 600/345 |
| 2007/0106135 A1 | 5/2007 | Sloan et al. | 600/322 |
| 2007/0142721 A1 | 6/2007 | Berner et al. | 600/347 |
| 2007/0197885 A1 | 8/2007 | Mah et al. | 600/310 |
| 2007/0264721 A1 | 11/2007 | Buck | 436/150 |
| 2008/0039702 A1 | 2/2008 | Hayter et al. | 600/345 |
| 2008/0056946 A1 | 3/2008 | Ahmad | 422/68.1 |
| 2008/0081977 A1 | 4/2008 | Hayter et al. | 600/365 |
| 2008/0098802 A1 | 5/2008 | Burke et al. | 73/61.61 |
| 2008/0101988 A1 | 5/2008 | Kang et al. | 422/58 |
| 2008/0121045 A1 | 5/2008 | Cole et al. | 73/861.08 |
| 2008/0161666 A1 | 7/2008 | Feldman et al. | 600/365 |
| 2008/0173552 A1 | 7/2008 | Wu et al. | 205/775 |
| 2008/0249385 A1 | 10/2008 | Phan | 600/347 |
| 2008/0255434 A1 | 10/2008 | Hayter et al. | 600/309 |
| 2008/0255437 A1 | 10/2008 | Hayter | 600/347 |
| 2008/0255808 A1 | 10/2008 | Hayter | 702/190 |
| 2008/0256048 A1 | 10/2008 | Hayter | 707/4 |
| 2008/0278331 A1 | 11/2008 | Hayter et al. | 340/573.1 |
| 2008/0288180 A1 | 11/2008 | Hayter et al. | 702/23 |
| 2008/0288204 A1 | 11/2008 | Hayter et al. | 702/130 |
| 2009/0030641 A1 | 1/2009 | Fjield et al. | 702/104 |
| 2009/0098657 A1 | 4/2009 | Blais et al. | 436/147 |
| 2009/0118604 A1 | 5/2009 | Phan et al. | 600/345 |
| 2009/0213360 A1 | 8/2009 | Braig et al. | 356/39 |
| 2009/0305319 A1 | 12/2009 | Baudenbacher et al. | 435/29 |
| 2009/0325205 A1 | 12/2009 | Fujii et al. | 435/14 |
| 2009/0325209 A1 | 12/2009 | West et al. | 435/25 |

FOREIGN PATENT DOCUMENTS

| | | |
|---|---|---|
| EP | 1909097 | 4/2008 |
| GB | 2204408 | 11/1988 |
| WO | WO 99/32881 | 7/1999 |
| WO | WO 00/40953 | 7/2000 |
| WO | WO 03/032138 | 4/2003 |
| WO | WO 03/082098 | 10/2003 |
| WO | WO 2004/113896 | 12/2004 |
| WO | WO 2004/113912 | 12/2004 |
| WO | WO 2004/113913 | 12/2004 |
| WO | WO 2005/001462 | 1/2005 |
| WO | WO 2005/003748 | 1/2005 |
| WO | WO 2005/008231 | 1/2005 |
| WO | WO 2005/108968 | 11/2005 |
| WO | WO 2006/109279 | 10/2006 |
| WO | WO 2008/130896 | 10/2008 |
| WO | WO 2008/138553 | 11/2008 |

OTHER PUBLICATIONS

Clemens Lasance, "The Seebeck Coefficient", Electronics Cooling Magazine, Nov. 1, 2006.*
Search Report corresponding to International Patent Application Serial No. PCT/US2010/039664, United States Patent Office; dated Oct. 5, 2010 (7 pages).

(56) References Cited

OTHER PUBLICATIONS

Written Opinion corresponding to International Patent Application Serial No. PCT/US2010/039664, United States Patent Office; dated Oct. 5, 2010 (8 pages).

* cited by examiner

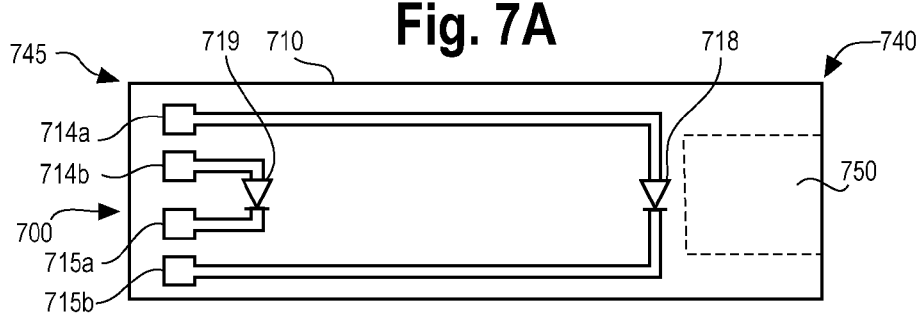
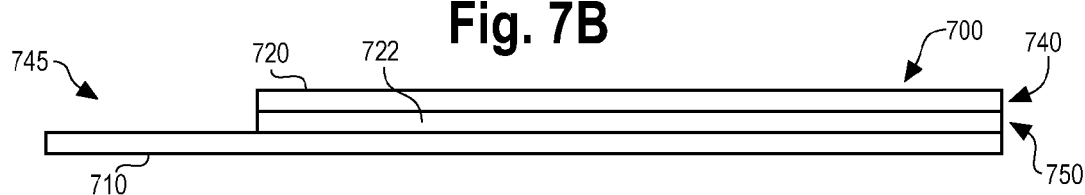
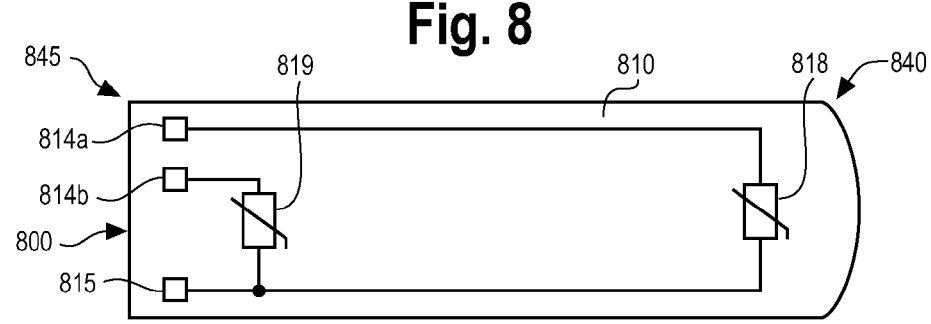

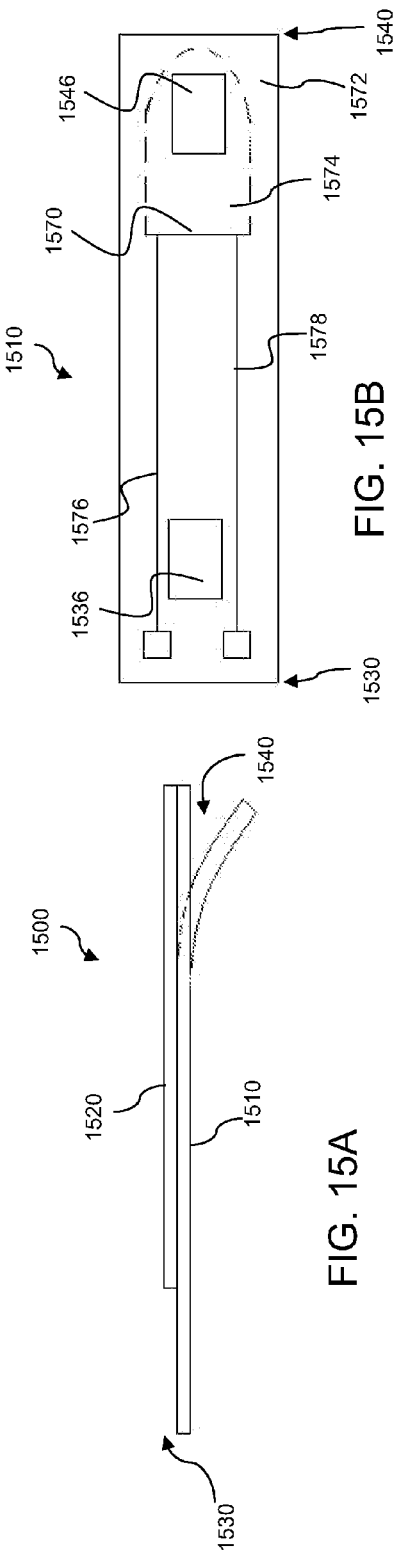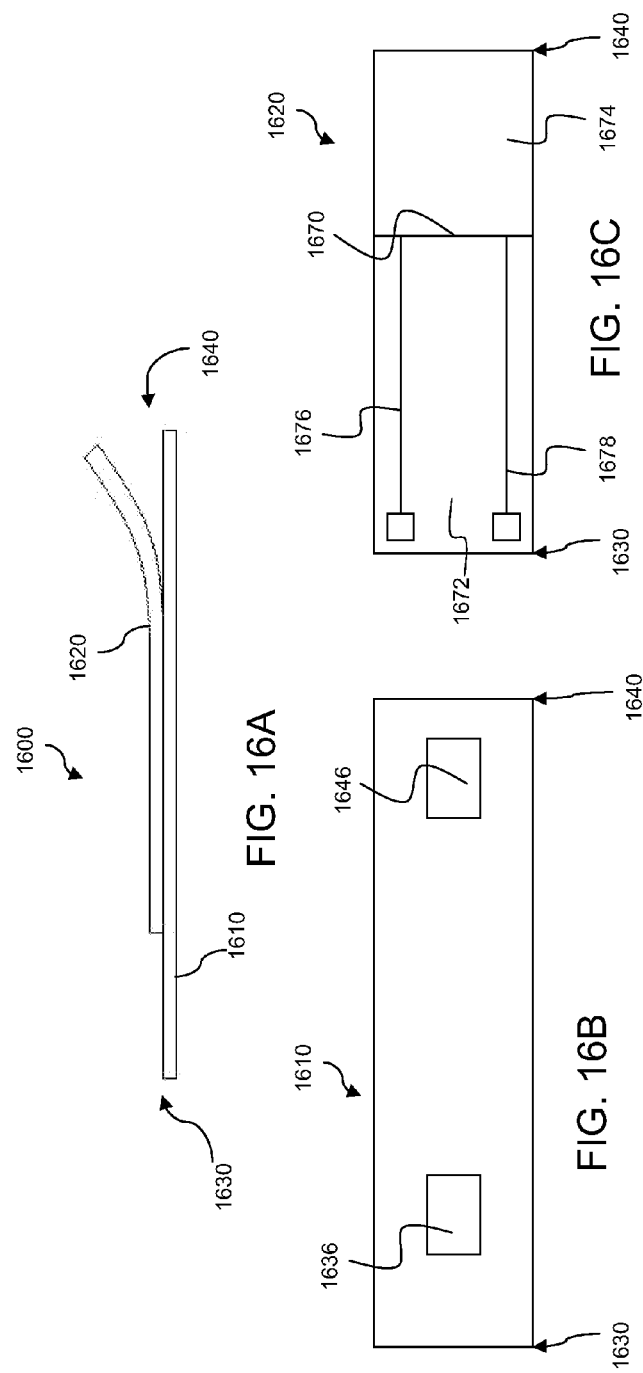

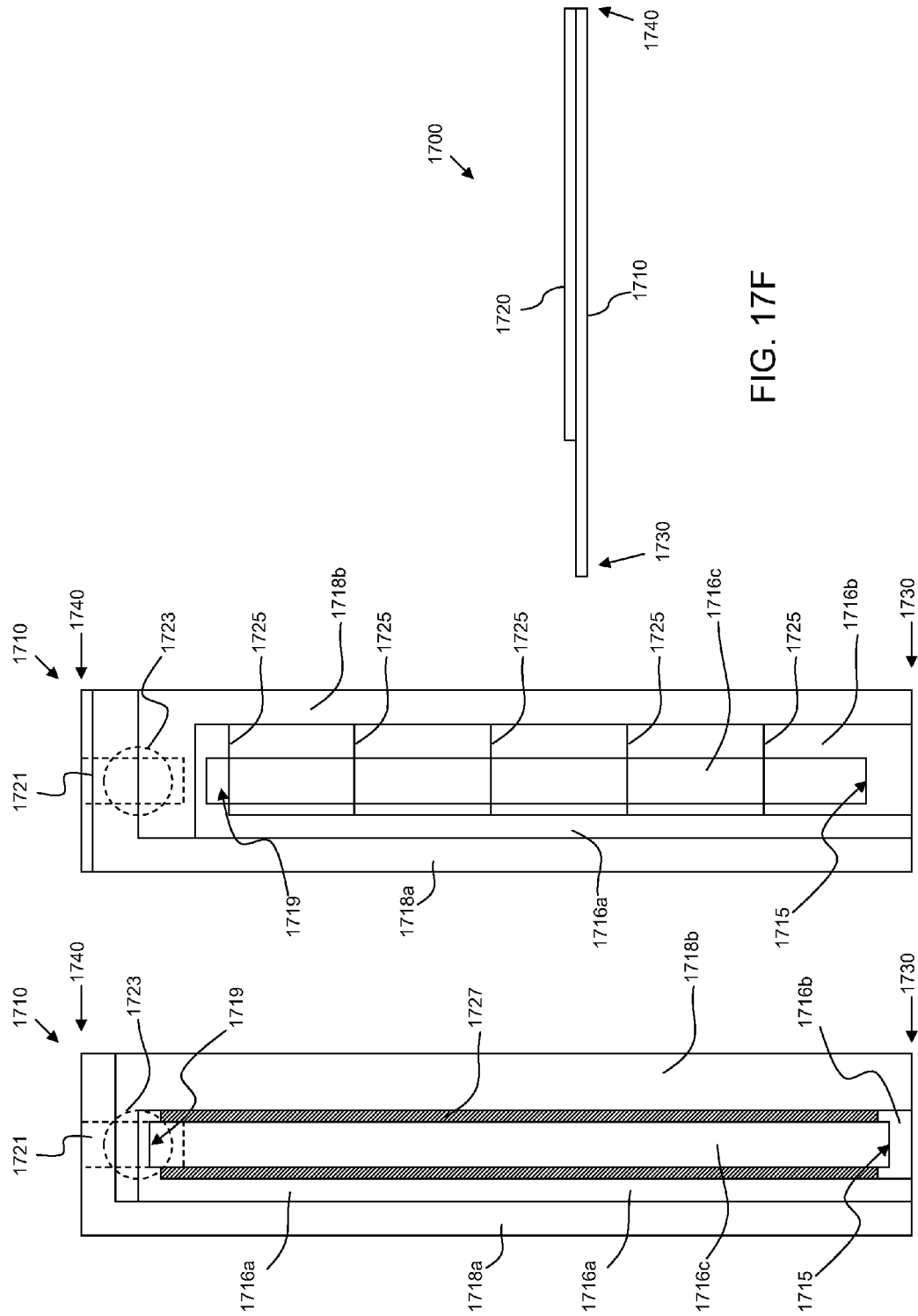

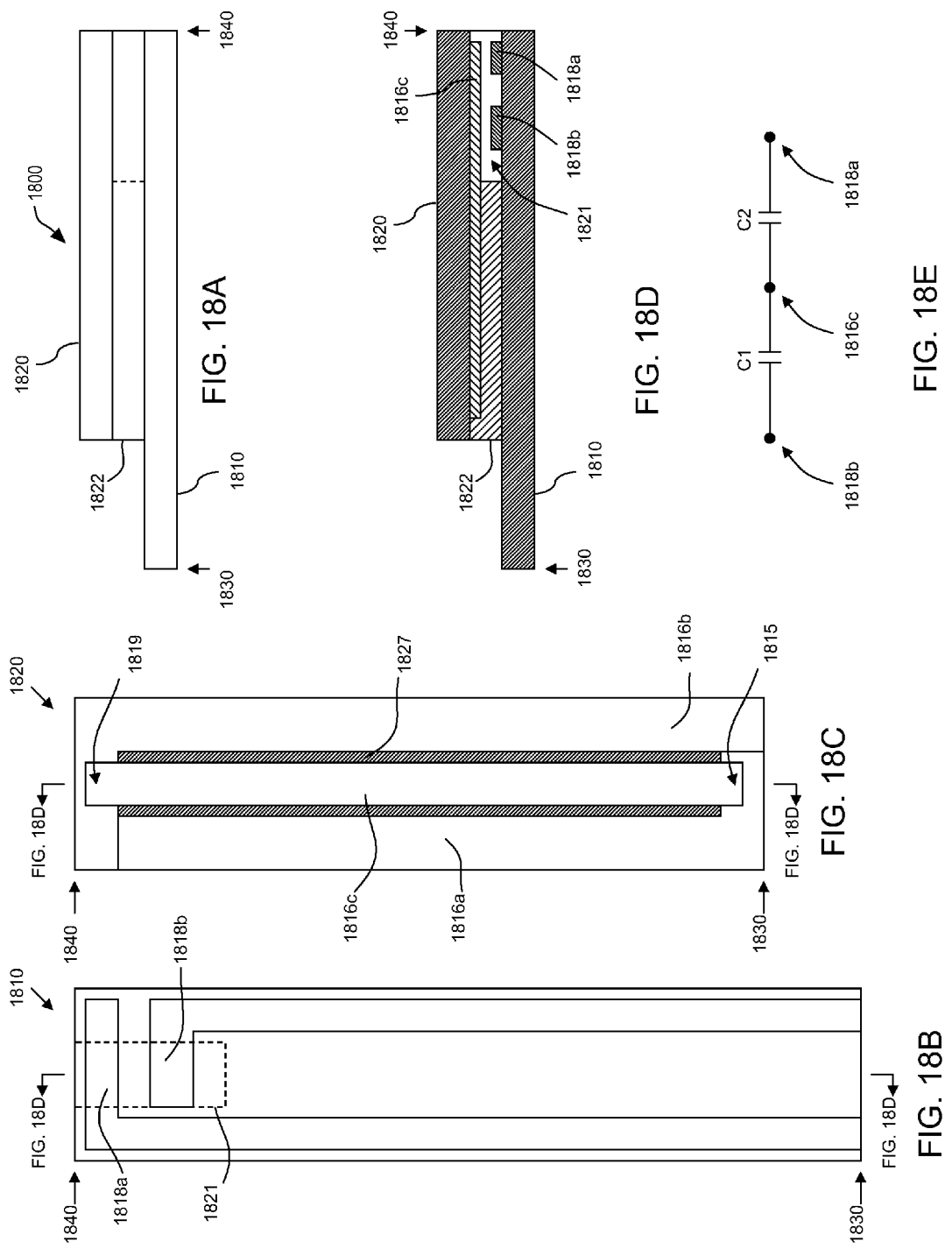

SYSTEM AND APPARATUS FOR DETERMINING TEMPERATURES IN A FLUID ANALYTE SYSTEM

CROSS-REFERENCE TO RELATED APPLICATIONS

This application is a divisional of U.S. patent application Ser. No. 14/094,434, filed Dec. 2, 2013, now allowed, which is a continuation of U.S. patent application Ser. No. 12/821,976, filed Jun. 23, 2010, now issued as U.S. Pat. No. 8,617,381, which claims priority to and the benefit of U.S. Provisional Patent Application No. 61/219,549, filed Jun. 23, 2009, each of which are hereby incorporated by reference herein in their entireties.

FIELD OF THE INVENTION

The present invention generally relates to fluid analyte systems, and more particularly, to the determination of differential temperatures in fluid analyte systems having one or more temperature sensing locations.

BACKGROUND OF THE INVENTION

The quantitative determination of analytes in body fluids is of great importance in the diagnoses and maintenance of certain physiological conditions. For example, lactate, cholesterol, and bilirubin should be monitored in certain individuals. In particular, determining glucose in body fluids is important to individuals with diabetes who must frequently check the glucose level in their blood to regulate the glucose intake in their diets. The results of such tests can be used to determine what, if any, insulin or other medication needs to be administered. In one type of testing system, test sensors are used to test a fluid such as a sample of blood.

Measurement of blood glucose concentration is typically based on a chemical reaction between blood glucose and a reagent. The chemical reaction and the resulting blood glucose reading as determined by a blood glucose meter is temperature sensitive. Therefore, a temperature sensor is typically placed inside the blood glucose meter. The ambient temperature and reagent temperature are then extracted using the temperature sensor readings. The calculation for blood glucose concentration in such meters typically assumes that the temperature of the reagent is the same as the temperature reading from a test sensor placed inside the meter. However, if the actual temperature of the reagent and the test sensor are different, the calculated blood glucose concentration decreases in accuracy. An increase in temperature or the presence of a heat source within a blood glucose meter will generally result in erroneous blood glucose measurements. Furthermore, the thermal properties of a blood glucose meter often render the system slow to respond to environmental changes such as a change in temperature.

SUMMARY OF THE INVENTION

According to one embodiment, a test sensor configured to determine a fluid analyte concentration of a fluid sample includes a test sensor body, a first conductive trace, a second conductive trace, and a third conductive trace. The test sensor body includes a first region that has a fluid-receiving area, a second region that is separate from the first region, and a first temperature sensing interface that is disposed at or adjacent to the fluid-receiving area. The fluid-receiving area is configured to receive a fluid sample and allow the fluid sample to be analyzed to determine a fluid analyte concentration. The first conductive trace is disposed on the test sensor body, and at least a portion of the first conductive trace is disposed in the first region. The second conductive trace is disposed on the test sensor body. The third conductive trace is also disposed on the test sensor body. The third conductive trace extends from the first region to the second region. The third conductive trace is connected to the first conductive trace at the first temperature sensing interface. The third conductive trace includes a different material than the first conductive trace such that a first thermocouple is formed at the first temperature sensing interface. The first thermocouple provides temperature data to assist in determining the fluid analyte concentration.

According to another embodiment, a test sensor for determining fluid analyte concentrations includes a first region, a second region, a first circuit, and a second circuit. The second region has a fluid-receiving area disposed therein. The first region is separate from the second region. The first circuit includes a first temperature element disposed in the first region. The second circuit includes a second temperature element disposed in the second region. The first temperature element and the second temperature element each include one or more resistive components. The resistive components of the first temperature element have a substantially equivalent resistance to the resistive components of the second temperature element. The first and second circuits are configured to receive excitation signals that energize the resistive components in the first and second temperature elements and further configured to output a signal that is indicative of a temperature difference between the first temperature element and the second temperature element.

According to another embodiment, a system for determining temperature differentials in a test sensor includes a test sensor and a meter. The test sensor has a fluid-receiving area and a connection end. The sensor includes a first temperature sensing device and a second temperature sensing device. The first temperature sensing device is disposed along a first circuit, and positioned adjacent to the fluid-receiving area. The second temperature sensing device is disposed along a second circuit, and positioned adjacent to the connection end. The second temperature sensing device has a resistance that is substantially equivalent to a resistance of the first temperature sensing device. The first circuit and the second circuit form a temperature differential circuit. The meter has an opening configured to connect with the connection end of the test sensor. The meter is configured to provide excitation signals to the temperature differential circuit. The meter includes a controller configured to receive output signals associated with the first and second temperature sensing devices. The controller is further configured to determine the differential resistance between the first and second resistive sensing devices based on the output signals. The differential resistance has a linear relationship with temperature.

According to another embodiment, a method for determining temperature differentials in a test sensor includes providing resistive components for a first temperature sensor and a second temperature sensor such that the resistive components of the first temperature sensor have a substantially equivalent resistance to the resistive components of the second temperature sensor. The method further includes receiving an excitation signal in the resistive components of the first temperature sensor and the second temperature sensor. The first temperature sensor and the second temperature sensor are associated with a temperature differential circuit. The second temperature sensor is disposed in a fluid-receiving area of the test sensor. The first temperature sensor is disposed in a region opposing the fluid-receiving area. The method further includes outputting a signal indicating a temperature difference between the first temperature sensor and the second temperature sensor.

According to another embodiment, a method for determining temperature differentials in a test sensor includes providing a first electrode and a second electrode disposed in a fluid-receiving area. The first electrode is connected to a first conductive trace, and the second electrode is connected to a second conductive trace. The method further includes providing a third conductive trace connected to one of the first electrode or the first conductive trace at a first temperature sensing interface disposed at or adjacent to the fluid-receiving area. The method further includes connecting a test sensor contact to the third conductive trace at a second temperature sensing interface disposed at the fluid-receiving area. The test sensor contact, the third conductive trace, and the second conductive trace include one of a metal or a carbon material. The test sensor contact and the second conductive trace are made of different materials than the third conductive trace thereby forming a first thermocouple at the first temperature sensing interface and a second thermocouple at the second temperature sensing interface.

According to another embodiment, a portable meter configured to monitor temperature changes associated with fluid sample collection includes a housing, a controller, and a differential temperature sensor. The housing defines an area for receiving a fluid sample. The controller is disposed within the housing. The differential temperature sensor is disposed on the housing. The differential temperature sensor includes a first electrode, a second electrode, a first conductor material, a second conductor material, and a third conductor material. The third conductor material includes a conductive material that is different from the first and second conductor materials. The first electrode and the second electrode are communicatively connected to the controller. The first electrode is connected to a first contact location on the first conductor material. The second electrode is connected to a second contact location on the second conductor material. The third conductor material is connected to the first conductor material at a third contact location and the second conductor material at a fourth contact location such that the third contact location forms a first temperature sensing interface and the fourth contact location forms a second temperature sensing interface.

According to another embodiment, a method for making a test sensor configured to determine a fluid analyte concentration of a fluid sample includes forming a first conductive trace on a test sensor body. The test sensor body includes a first region that has a fluid-receiving area, a second region that is separate from the first region, and a first temperature sensing interface that is disposed at or adjacent to the fluid-receiving area. The fluid-receiving area is configured to receive a fluid sample and allow the fluid sample to be analyzed to determine a fluid analyte concentration. At least a portion of the first conductive trace is disposed in the first region. The method further includes forming a second conductive trace on the test sensor body, and forming a third conductive trace on the test sensor body. The third conductive trace extends from the first region to the second region. The third conductive trace is connected to the first conductive trace at the first temperature sensing interface. The third conductive trace includes a different material than the first conductive trace such that a first thermocouple is formed at the first temperature sensing interface. The thermocouple provides temperature data to assist in determining the fluid analyte concentration.

According to another embodiment, a method for making a test sensor configured to determine a fluid analyte concentration of a fluid sample includes forming a metal layer on a substrate, attaching the substrate with the metal layer to a test sensor body, forming a first conductive trace on the metal layer, forming a second conductive trace on the metal layer, and forming a third conductive trace on the metal layer. The test sensor body includes a first region that has a fluid-receiving area, a second region that is separate from the first region, and a first temperature sensing interface that is disposed at or adjacent to the fluid-receiving area. The fluid-receiving area is configured to receive a fluid sample and allow the fluid sample to be analyzed to determine a fluid analyte concentration. At least a portion of the first conductive trace is disposed in the first region. The third conductive trace extends from the first region to the second region. The third conductive trace is connected to the first conductive trace at the first temperature sensing interface. The third conductive trace includes a different material than the first conductive trace such that a first thermocouple is formed at the first temperature sensing interface. The thermocouple provides temperature data to assist in determining the fluid analyte concentration.

According to another embodiment, a test sensor for determining fluid analyte concentrations includes a first region, a second region, a first circuit, and a second circuit. The second region has a fluid-receiving area disposed therein. The first region is separate from the second region. The first circuit includes a first temperature element disposed in the first region. The second circuit includes a second temperature element disposed in the second region. The first temperature element and the second temperature element each include one or more diodes. The first and second circuits are configured to receive excitation signals that energize the diodes in the first and second temperature elements and further configured to output a signal that is indicative of a temperature difference between the first temperature element and the second temperature element.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIG. 7A illustrates a test sensor for determining differential temperatures using diodes according to another embodiment.

FIG. 7B illustrates a side view of the test sensor in FIG. 7A.

FIG. 8 illustrates a test sensor for determining differential temperatures using resistors according to another embodiment.

FIG. 15A illustrates a side view for a test sensor for determining differential temperatures according to another embodiment.

FIG. 15B illustrates a top view of a base for the test sensor in FIG. 15A.

FIG. 16A illustrates a side view for a test sensor for determining differential temperatures according to another embodiment.

FIG. 16B illustrates a top view of a base for the test sensor in FIG. 16A.

FIG. 16C illustrates a bottom view of a lid for the test sensor in FIG. 16A.

FIGS. 17A-E illustrate a top view of a base for a test sensor for determining differential temperatures using one or more thermocouples according to alternative embodiments.

FIG. 17F illustrates a side view of the test sensor including the bases illustrated in FIGS. 17A-E.

FIG. 18A illustrates a side view of a test sensor for determining differential temperatures and measuring capacitance of a sample fluid using one or more thermocouples and electrodes according to an alternative embodiment.

FIG. 18B illustrates a top view of a base for the test sensor illustrated in FIG. 18A.

FIG. 18C illustrates a bottom view of a lid for the test sensor illustrated in FIG. 18A.

FIG. 18D illustrates a sectional side view through a longitudinal axis of the test sensor illustrated in FIGS. 18A-C.

FIG. 18E illustrates a circuit diagram for determining capacitance according to the embodiment illustrated in FIGS. 18A-D.

Figure 1:
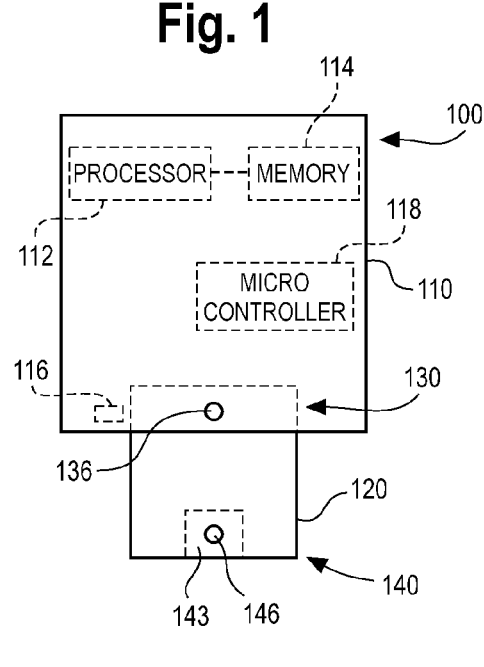
FIG. 1 illustrates a fluid analyte system including a meter and a test sensor according to one embodiment.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents, and alternatives falling within the spirit and scope of the invention.

DETAILED DESCRIPTION

Generally, a test sensor is employed to collect a blood sample, and a blood glucose meter measures a reaction between the glucose in the sample with a reagent on the test sensor to calculate a corresponding blood glucose concentration. The temperature of the reagent affects the reaction between the glucose and the reagent. As such, the temperature of the reagent also affects the blood glucose concentration calculated by the blood glucose meter. The temperature of the reagent is assumed to be substantially equal to the ambient temperature in or surrounding the meter. Temperature sensing elements in the blood glucose meter can provide an estimate of the ambient temperature, which can then be used in the calculation of the blood glucose concentration. However, the blood glucose meter includes various heat-generating elements that can cause the temperature measured by the temperature sensing elements in the meter to differ from the ambient temperature. When the temperature measured by the temperature sensing elements do not provide an accurate estimate of the ambient temperature, inaccuracies are introduced into the determination of the blood glucose concentration.

To achieve more accurate determinations of the blood glucose concentration, a temperature differential may be calculated to account for the discrepancy between the temperature measured by the temperature sensing elements and the ambient temperature. According to aspects of the present invention, varying materials are employed to provide the test sensor with sensing elements that determine the temperature differential. In some embodiments, a first sensing element is disposed at or near the reagent, and a second sensing element is disposed at or near the end of the test sensor received by the blood glucose meter. The test sensor also includes one or more conductive pathways, or traces, that extend between and connect the first and second sensing elements. In general, printed circuit board technology employing selected materials mechanically supports and electronically connects components using traces formed on a non-conductive substrate defining the test sensor.

Figure 5A:
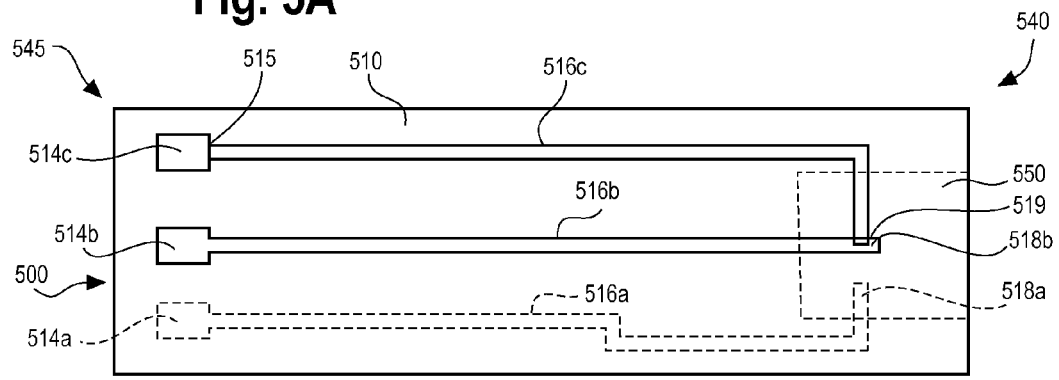
FIG. 5A illustrates a test sensor for determining differential temperatures using one or more thermocouples according to one embodiment.
Figure 5B:
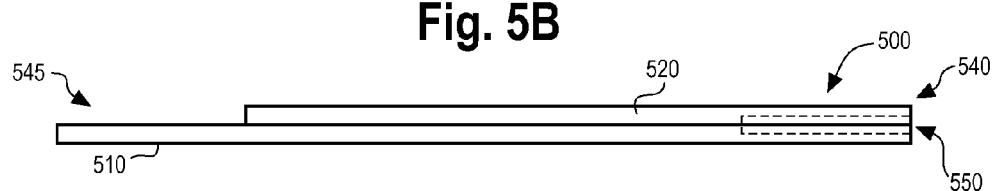
FIG. 5B is a side view of the test sensor in FIG. 5A.
Figure 5C:
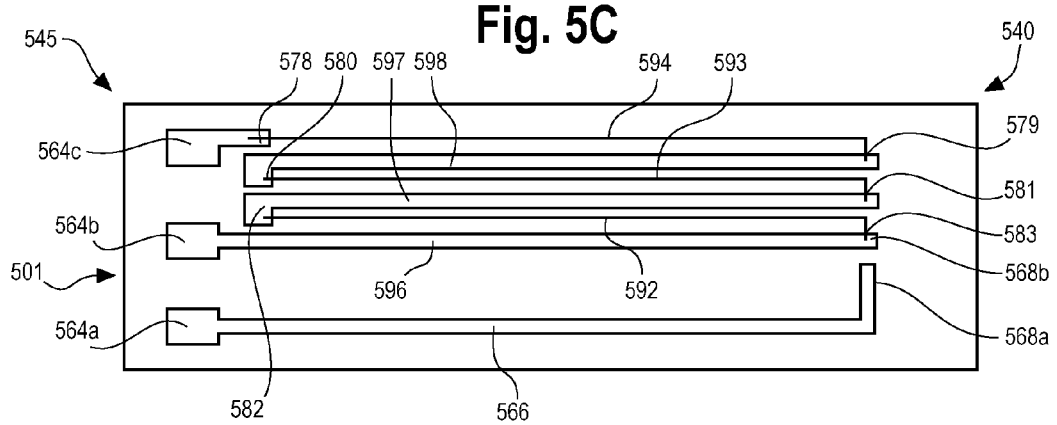
FIG. 5C illustrates a test sensor for determining differential temperatures using one or more thermocouples according to another embodiment.

Embodiments of test sensors configured to measure differential temperature are illustrated in FIGS. 5A-C. Systems that may employ these test sensors are described further below, for example, in connection with FIGS. 1-2.

FIGS. 5A-5C illustrate an electrochemical test sensor 500 for determining differential temperatures using one or more thermocouples according to various embodiments. The test sensor 500 is adapted to receive a sample fluid. The test sensor 500 includes a base 510, a capillary channel, and a plurality of electrodes 518a, 518b. A fluid-receiving end 540 of the test sensor 500 includes the capillary channel (e.g., after a lid 520 is placed over the base 510). The plurality of electrodes includes a counter electrode 518a and a working (measuring) electrode 518b. The electrochemical test sensor 500 may also include additional electrodes such as, for example, an auxiliary electrode, a trigger electrode, a hematocrit electrode, combinations thereof, and/or the like. The electrodes 518a, 518b are coupled to a plurality of conductive leads 516a, 516b (e.g., conductive traces), which, in the illustrated embodiment, terminate respectively into a larger area designated as test-sensor contacts 514a, 514b. The capillary channel is generally located in the fluid-receiving area 550. It is contemplated that other electrochemical test sensor configurations can be employed.

The fluid-receiving area 550 includes at least one reagent for converting the analyte of interest (e.g., glucose) in the sample fluid (e.g., blood) into a chemical species that is electrochemically measurable, in terms of the electrical current it produces, by the components of the electrode pattern. The reagent typically contains an enzyme such as, for example, glucose oxidase, which reacts with the analyte and with an electron acceptor such as a ferricyanide salt to produce an electrochemically measurable species that can be detected by the electrodes. It is contemplated that other enzymes may be used to react with glucose such as, for example, glucose dehydrogenase. If the concentration of another analyte is to be determined, an appropriate enzyme is selected to react with the analyte.

A sample fluid (e.g., blood) may be applied to the fluid-receiving area 550. The sample fluid reacts with the at least one reagent. After reacting with the reagent and in conjunction with the plurality of electrodes, the sample fluid produces electrical signals that assist in determining the analyte concentration. The conductive leads 516a, 516b carry the electrical signal back toward a second opposing end 545 (e.g., connection end or region) of the test sensor 500 where the test-sensor contacts 514a, 514b transmit the electrical signals to the meter.

The test sensor 500 further includes a conductive trace 516c that is connected to the electrode 518b at a first temperature sensing interface 519 (e.g., a sensing junction or a "hot junction"). The conductive trace 516c is also connected to a test-sensor contact 514c at a second temperature sensing interface 515 (e.g., a reference junction or a "cold junction"). The conductive trace 516c is made of a conductive material that is different from the conductive materials used to make the test-sensor contact 514c and the electrode 518b. By using a material for the conductive trace 516c that is different than the conductive material used for the electrode 518b and the test-sensor contact 514c, a first thermocouple is formed at the first temperature sensing interface 519 and a second thermocouple is formed at the second temperature sensing interface 515. The two thermocouples assist in determining the differential temperature between the interfaces 515, 519 based on thermoelectric principles (e.g., the Seebeck effect).

In certain embodiments, the conductive trace 516c includes a conductive carbon-based material (e.g., a carbon paste, graphite tape, carbon fibers, combinations thereof, and/or the like) while the test-sensor contact 514c and the electrode 518b include a noble metal (e.g., gold, platinum, palladium, combinations thereof, and/or the like). In alternative embodiments, the conductive trace 516c can include a metal while the test-sensor contact 514c and the electrode 518b include a carbon-based material. It is contemplated that any other conductive materials or compounds can be used for conductive trace 516c, the test-sensor contact 514c, and the electrode 518b provided the materials or compounds used for the conductive trace 516c are different than the materials or compounds used for the test-sensor contact 514c and/or the electrode 518b.

Similar to the test-sensor contacts 514a, 514b, the test sensor contact 514c transfers electrical signals generated by the thermocouples at the interfaces 515, 519 to the meter. The electrical signals correlate to the differential temperature between the interfaces 515, 519. That is, the change in voltage across the thermocouples in the test sensor 500 may be proportional to or may be indicative of a change in temperature (e.g., differential temperature) between the first interface 519 and the second interface 515.

According to thermoelectric principles, the materials used to form the thermocouples (i.e., the first intersection 519 and the second intersection 515) directly affects the voltage levels that can be generated by the thermocouples. In general, the output electrical signal through the test-sensor contact 514c can be several microvolts per degree Celsius differential temperature. For example, in one embodiment, the relationship between the change in voltage and the change in temperature is approximately 1 to 10 microvolts per degree Celsius for voltage measurements made between test-sensor contacts 514b and 514c.

It is contemplated that, in some embodiments, the portion(s) of a connector in a meter that contact the respective test-sensor contacts 514a, 514b, 514c can be made from the same material as the test-sensor contacts 514a, 514b, 514c to mitigate problems that may otherwise arise if additional thermocouples were created between the connector and the test-sensor contacts 514a, 514b, 514c due to the connection(s) of dissimilar conductive materials.

Advantageously, in addition to determining differential temperatures, the output electrical signal through the test-sensor contact 514c can also be used as a low voltage power source. For example, the voltage generated by the thermocouple(s) can be used to test a microchip or a processor in the meter. As explained above and in further detail below, the materials used to form the thermocouple or the number of junctions provided to form a thermopile can be selected to achieve a desired voltage (relative to temperature differential) of the output signal from the test sensor through the test-sensor contact 514c.

As described above, more accurate determinations of the blood glucose concentration are achieved when a temperature differential is calculated to account for the discrepancy between the temperature measured by the thermocouple at the first interface 519 and the thermocouple at the second interface 515. The first interface 519 can be located at or near an area where the temperature is desired to be determined. For example, the first interface 519 can be located at or near the site of the electrochemical reaction between the electrodes, the sample fluid and the reagent. The second interface 515 can be located at or near a location where the temperature is known (e.g., near a separate temperature sensor). For example, in the illustrated embodiment, the second interface 515 is located near the second opposing end 545 (i.e., near a meter, which may include the separate temperature sensor). The temperature of the area where the temperature is desired to be determined (e.g., site of the electrochemical reaction) can then be calculated as the known temperature plus or minus the differential temperature between the first interface 519 and the second interface 515.

In certain embodiments, a fluid-analyte meter is configured to operate at approximately 25 degrees Celsius with thermocouple(s) or other differential temperature sensors (such as the differential temperature sensors illustrated and described below for FIGS. 7A-8) providing a differential temperature range of approximately plus or minus 10 degrees Celsius. For this embodiment, the temperature range of the meter would be from approximately 15 to 35 degrees Celsius. In certain embodiments, it can be beneficial to move the operating range of a meter by, for example, increasing the reference temperature to a value higher than 25 degrees Celsius (e.g., 35 degrees Celsius). The increase in the reference temperature can be accomplished by heating the meter to the desired temperature. Assuming the differential temperature range stays the same, the temperature range can be effectively shifted to a range of approximately 25 to 45 degrees Celsius. Other temperature ranges are contemplated including a higher or lower reference temperature (e.g., between approximately 15 and 35 degrees Celsius) and a higher or lower differential temperature range (e.g., approximately plus or minus 5 degrees up to approximately plus or minus 20 degrees Celsius).

In embodiments where the first interface 519 is located at the site of the electrochemical reaction (i.e., the reaction between the electrodes, the reagent and the sample fluid), electrical interference may be introduced to the thermocouple at the first interface 519 by the electrodes 518a, 518b. To minimize such interference, it can be desirable for the first interface 519 to be isolated or insulated from the electrochemical circuit formed with the sample fluid (i.e., the circuit formed by the working electrode, the counter electrode, the reagent, and the sample fluid). Accordingly, in certain embodiments, the first interface 519 is coated by an insulating or thermally conductive material to provide the isolation or insulation of the first interface 519 from the electrochemical circuit. Advantageously, however, if materials used to form the thermocouple are non-interfering catalysts (e.g., electrochemically compatible) such as, for example, carbon and a noble metal, interference issues are mitigated.

In certain embodiments, the conductive lead 516c and the electrode 518b or the test-sensor contact 514c may be mechanically bonded or thermally pressed together at the first interface 519 and/or the second interface 515 to form the thermocouple(s) in the test sensor 500. For example, lasers may be used to melt the various metal layers together in making the strip. It is contemplated that other forms of bonding may also be used at the first interface 519 and/or the second interface 515 such as a bond using carbon paste to hold a conductive lead to an electrode, contact, or to a conductive trace. For example, the connections can be formed using conductive glue, melting, forming, overlaying (e.g., physical contact), or as otherwise known in the art.

It can be desirable for the thermocouple interfaces between the two conductive materials to be fabricated where the junction or interface is kept as small as possible. For example, it is contemplated that the area of the junction or interface can be approximately 0.1 mm$^2$ to approximately 1.0 mm$^2$. Further, it can be desirable for the resistance in the conductive traces forming the thermocouples to be low, such as less than approximately 500 ohms, less than approximately 100 ohms, or less than approximately 50 ohms to mitigate the loss of voltage provided from the thermocouples to the meter.

While the thermocouple at the first interface 519 is formed by the working electrode 518b and the conductive trace 516c in FIG. 5A, it is contemplated that, in alternative embodiments, the first interface 519 can be formed by a connection between the conductive trace 516c and the counter electrode 518a instead.

According to other alternative embodiments, neither the counter electrode 518a nor the working electrode 518a are used to form the first interface 519 with the conductive trace 516c. Rather, a separate conductive trace can be provided to contact the first conductive trace 516c and form the first interface 519, provided the conductive traces are made of different conductive materials or compounds. Non-limiting examples of test sensors including a separate conductive trace that is distinct from the working and counter electrodes for forming a thermocouple with a first conductive trace at the first interface are illustrated and described below with respect to FIGS. 17A-18E.

Similarly, the thermocouple at the second interface 515 can be formed by providing a separate conductive trace connected to the first conductive trace 516c instead of a test-sensor contact 514c connected to the first conductive trace 516c. Non-limiting examples of such embodiments are also illustrated and described below with respect to FIGS. 17A-18E. In still other alternative embodiments, the test-sensor contact 514c can be made from the same material as the first conductive trace 516c, and the thermocouple at the second interface 515 can be formed by a connection between the test-sensor contact 514c and a connector disposed inside a meter provided that the connector is made from a different material than the test-sensor contact 514c (and the first conductive trace 516c). It is contemplated that the geometry and physical characteristics of the contact sensor 514c can be changed to reflect the cross-sectional geometry and material characteristics of the conductive lead 516c.

While the counter electrode 518a, the working electrode 518b, the first interface 519, and the second interface 515 are located on the base 510 of the test sensor 500 illustrated in FIG. 5A, it is contemplated that, according to alternative embodiments, these components can be located on or in any layer (i.e., a base, a spacer, and/or a lid) of a test sensor. For example, in certain embodiments, the counter electrode 518a can be located on the base 510 while the working electrode 518b and the conductive trace 516c (and, thus, the first interface 519 formed by a connection thereof) are located on the lid 520 of a test sensor. Another non-limiting example of such alternative configurations is illustrated and described below with respect to FIGS. 18A-E. It is still further contemplated that the first interface 519 can be formed on a reagent layer located on a lid, a spacer, or a base of a test sensor.

While the test sensor illustrated and describe above for FIG. 5A includes two thermocouples (e.g., at the first interface and the second interface), it is contemplated that more than two thermocouples can be provided on a test sensor. Providing additional thermocouples at one or more locations on a test sensor assists in collecting additional temperature data and, thus, increases accuracy or versatility of temperature measurement.

Other benefits of the differential temperature sensor embodiments described herein are that temperature differences between a test sample, a test sensor, the fluid-analyte meter, and other areas of concern can be readily determined with a high level of accuracy. Furthermore, the differential temperature sensors allow temperature effects to be readily compensated for in determining analyte concentrations. Furthermore, the concepts described herein can be particularly desirable for disposable-type applications or for situations where multiple locations may be assessed for temperature effects. The efficiency of the design can be useful for high-volume fabrication techniques for disposable-type test sensor applications.

FIG. 5C illustrates an embodiment of a test sensor 501 having multiple junctions or thermocouple interface pairs. The arrangement of multiple interface pairs in a test sensor can increase the sensitivity of the differential temperature measurements. The test sensor 501 includes a plurality of electrodes 568a, 568b and a plurality of conductive traces 566, 592, 593, 594, 596, 597, 598. In certain embodiments, conductive traces 592, 593, 594 may be fabricated from carbon materials and conductive traces 596, 597, 598 may be fabricated from either palladium, gold, or similar metal materials. Several hot junctions or thermocouple interfaces are formed in series at interfaces 579, 581, 583. Furthermore, several cold junctions are formed at interfaces 578, 580, 582. Conductive traces 566, 596, 594 are respectively connected to contacts 564a, 564b, 564c. Similar to test-sensor contacts 514a, 514b, 514c, contacts 564a, 564b, 564c transfer electrical signals generated by the thermocouples to the meter. The electrical signals correlate to the differential temperature between interface pairs 578, 579 and 580, 581 and 582, 583. It is contemplated that in certain embodiments that the thermocouple interfaces are configured to be isothermal, such as the configurations illustrated in FIG. 5C. It is further contemplated that more or fewer thermocouple interface pairs than are illustrated in FIG. 5C can be fabricated into a test sensor as need to meet a desired sensitivity in temperature measurements.

In certain embodiments, a sample fluid (e.g., blood) may be applied to form a connection across electrodes 568a, 568b. The sample fluid may react with a reagent disposed near electrodes 568a, 568b. After reacting with the reagent and in association with the plurality of electrodes, the sample fluid may produce or transduce signals that assist in determining the analyte concentration of the sample fluid.

FIG. 5B is a side view of the test sensor in FIG. 5A. FIG. 5B is also similar to an exemplary side view embodiment for the test sensor in FIG. 5C. The test sensor 500 includes the lid 520 and the base 510. The base 510 and the lid 520 may be made from a variety of materials such as polymeric materials. Non-limiting examples of polymeric materials that may be used to form the base 510 and the 520 include polycarbonate, polyethylene terephthalate (PET), polyethylene naphthalate (PEN), polyimide, and combinations thereof. It is contemplated that other materials may also be used in forming the base 510 and the lid 520.

To form the test sensor 500 or the test sensor 501 of FIGS. 5A-5C, the base 510 and the lid 520 are attached by, for example, a pressure and/or heat sensitive adhesive. When the base 510 and the lid 520 are attached, a fluid-receiving area 550 can be formed. The fluid-receiving area 550 provides a flow path for introducing the sample fluid into the test sensor 500 or the test sensor 501.

Figure 6:
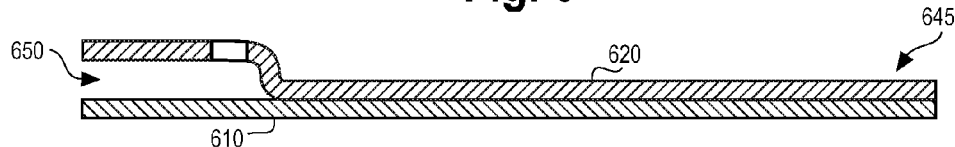
FIG. 6 is a cross-sectional view of a test sensor according to another embodiment.

FIG. 6 is a cross-sectional view of a test sensor according to another embodiment. It is contemplated that the test sensors of the exemplary embodiments presented herein may be formed with a base and a lid in which the lid has an offset. In one such embodiment, a lid may be formed with a convex opening that is adapted to receive a fluid. A non-limiting example of such a test sensor is shown in FIG. 6. The test sensor includes a base 610 and a lid 620. When the lid 620 is attached to the base 610, a fluid-receiving area 650 is formed that is adapted to receive fluid for testing along with an opposing end 645 (e.g., connection end) that may interface with a meter.

It is contemplated that spacer elements may also be disposed between the base and the lid elements illustrated in FIGS. 5B and 6. One example of such a spacer element is illustrated below in FIG. 7B.

FIGS. 7A-7B illustrate an electrochemical test sensor 700 for determining differential temperatures using diodes according to another embodiment. The test sensor 700 includes a base 710, a capillary channel, and a plurality of circuits each including diodes 718, 719. A fluid-receiving end 740 (e.g., test end) of the test sensor 700 includes the capillary channel (e.g., after a lid 720 is placed over a spacer 722). The first of the plurality of circuits includes a test-sensor contact 714a connected to a diode 718 and a test-sensor contact 715b. In certain embodiments, it is desirable for the diode 718 to be located within the base 710 at or in close proximity to a fluid-receiving area 750 of the adjacent spacer 722 or lid 720 as illustrated in FIG. 7A. The second of the plurality of circuits includes a test-sensor contact 714b connected to the diode 719 and test-sensor contact 715a. It can be desirable for diode 719 to be located within the base 710 at or in close proximity to a connection end 745 where the test sensor 700 connects or interfaces with a meter. Test sensor contacts 714a, 714b, 715a, 715b can be coupled to diodes 718, 719 by a plurality of conductive leads (e.g., conductive traces) that complete the individual circuits. The conductive leads may be made from a conductive non-metal material (e.g., carbon-based materials) or from metal materials (e.g., copper, iron, noble metals such as gold, platinum, palladium, or silver). The capillary channel is generally located in the fluid-receiving area 750. It is contemplated that other electrochemical test sensor configurations may be employed.

Diode-type temperature sensors, such as the diodes 718, 719, are based on the relationship between temperature and a threshold voltage of a diode circuit, and the determination of a temperature dependent current-voltage curve. With a fixed excitation voltage, differential temperature can be determined by measuring leakage current through the circuit.

The diodes 718, 719 define the temperature sensing elements of the first circuit and the second circuit that are used to determine a differential temperature. Each diode 718, 719 effectively introduces a resistance into the respective circuits illustrated in FIG. 7A. The diodes 718, 719, the conductive leads, and the test-sensor contacts 714a, 714b, 715a, 715b can be fabricated onto the same base strip element. The diodes 718, 719 can be, for example, semiconductor p-n junction diodes, light-emitting diodes (LED) or organic light-emitting diodes (OLED).

It can be desirable for the diodes 718, 719 to be matched. Matching can include the diodes 718, 719 each having substantially the same leakage current characteristics when fixed excitation voltages are applied across the diodes 718, 719. Matching can further include that diodes 718, 719 also have substantially the same physical configuration (e.g., topology) and material properties.

It is contemplated that in certain embodiments the conductive traces individually associated with the diodes 718, 719 have substantially the same equivalent resistance to each other. The current in each of the circuits illustrated in FIG. 7A is temperature dependent. If the circuit including the diode 718 has substantially the same leakage current characteristics as the circuit including the diode 719, differential temperature can be directly determined by applying a fixed excitation voltage to the diode circuit, looking for changes in current (e.g. leakage current), and then correlating the current change with temperature. It is therefore contemplated that a differential temperature test sensor system using diodes can also be called a differential current measurement circuit, where a differential temperature to current relationship allows direct correlation of temperature to current.

The use of a diode in a test sensor offers additional benefits in addition to determining differential temperature. An LED or OLED in a sensor strip also provides lighting functions to the strip. For example, an LED in the sensor strip can mark the location on the sensor where a user should place the blood sample. As another example, after an analyte concentration is determined for a fluid sample, one or more of the LEDs in the test sensor can light up in different combinations and/or colors to indicate the test result. It is also contemplated that the number or result of the analyte concentration test can be displayed directly on a diode (e.g., OLED) on the test sensor. Furthermore, the diodes in the test sensor can be energized using a battery or alternating current (AC) to apply the current to the temperature sensor circuits. For a circuit energized using AC power, the use of a diode can allow the collection of additional data related to temperature.

FIG. 7B illustrates a side view of the test sensor 700 in FIG. 7A. The test sensor 700 of FIG. 7B includes the lid 720, the spacer 722, and the base 710. The base 710, the lid 720, and the spacer 722 may be made from a variety of materials such as polymeric materials (e.g., polycarbonate, PET, PEN, polyimide, or combinations thereof). To form the test sensor 700, the base 710, the spacer 722, and the lid 720 are attached by, for example, an adhesive or heat sealing. When the base 710, the lid 720, and the spacer 722 are attached, a fluid-receiving area 750 is formed at the fluid-receiving end 740 (e.g., test end) of the test sensor 700. The fluid-receiving area 750 provides a flow path for introducing the fluid sample into the test sensor 700.

It is contemplated that in certain embodiments, a differential temperature sensing arrangement includes two temperature sensing elements configured to allow the differential temperature to be measured directly. In one non-limiting example, two resistance temperature detectors (RTD) are included in the same circuit and the differential voltage over the circuit can be measured based on the same excitation current being applied over both RTDs. Different types or RTDs can be used including thin-film, wire-wound, or coil type RTDs. It is desirable for the resistance of the RTD element to vary linearly with temperature.

For the thin-film RTD, a layer of platinum can be adhered or attached to a substrate, such as a ceramic substrate. In certain embodiments, the thickness of the platinum film can be in the range of approximately 1 micrometer. In one embodiment, the film is approximately 0.1 micrometers thick. It is contemplated that in certain embodiments the thickness of the film can range from approximately 0.04 micrometers to approximately 1 micrometer. It is contemplated that other materials may be used to construct the RTD, including other noble metals (e.g., palladium, gold, or silver), copper, iron, silicon carbide, and/or carbon. Platinum offers the advantage of high accuracy, low drift, a wide operating range, and better suitability in precision applications such as fluid analyte systems for medical applications.

For wire-wound or coil-type RTD embodiments, a wire coil may be supported within a sealed housing or in a ceramic cylinder. In certain embodiments, a wire may also be encapsulated in glass or a similar material with the wire around the glass core with the glass fused homogeneously around the wire.

It is further contemplated that a thermistor may also be used as a temperature sensor in place of an RTD. A thermistor can be desirable for higher precision temperature measurements over a more limited temperature range.

FIG. 8 illustrates an electrochemical test sensor 800 for determining differential temperatures using resistors according to another embodiment. The test sensor 800 includes a base 810, a capillary channel, and a plurality of circuits each including a resistance temperature detector (RTD) 818, 819, or other type of temperature-influenced resistors such as a thermistor. The test sensor 800 includes a fluid-receiving end 840 and a connection end 845. The first of the plurality of circuits includes a test-sensor contact 814a connected to an RTD 818 and a test-sensor contact 815. In certain embodiments it is desirable for the RTD 818 to be disposed in a strip or base 810 of the test sensor at or in close proximity to the fluid-receiving end 840 as illustrated in FIG. 8. Alternatively, the RTD 818 may be positioned similar to the diode 718 in the test sensor configuration of FIG. 7A. The second of the plurality of circuits includes a test-sensor contact 814b connected to an RTD 819 and test-sensor contact 815a. It can be desirable for the RTD 819 to be disposed in the base 810 at or in close proximity to the connection end 845 where the test sensor 800 connects or interfaces with a meter. Test sensor contacts 814a, 814b, 815 can be coupled to the RTDs 818, 819 by a plurality of conductive leads (e.g., conductive traces) that complete the individual circuits. Both RTD circuits can terminate at a common working test-sensor contact 815 as illustrated in FIG. 8 or the circuits can terminate at dedicated test-sensor contacts similar to the working test-sensor contact configuration illustrated in FIG. 7A. The conductive leads may be made from a conductive non-metal material (e.g., carbon-based materials, silicon carbide fibers) or from metal materials (e.g., copper, iron, noble metals such as gold, platinum, palladium, or silver). It is further contemplated that in certain embodiments the differential temperature sensors are made with laser-trimmed RTD materials such as palladium, gold, silver, or platinum. The differential temperature sensors can also comprise other conducting materials including other metals or conducting ceramics such as silicon carbide. Other electrochemical test sensor configurations may also be employed.

In certain embodiments, the electronics associated with the test sensor 800 can be fabricated on a printed circuit board. The RTD 818 and the RTD 819 can be laser etched onto a thin film of a noble metal material (e.g., platinum, palladium, gold, silver) already fabricated onto the strip. It is contemplated that the RTD 818 and the RTD 819 be matched such that both resistance temperature detectors have the same resistance. The RTD 818 and the RTD 819 can further be matched by also having substantially the same physical configuration (e.g., the same topology) and material properties. It is contemplated that in certain embodiments the circuit formed with the RTD 818 has a substantially equivalent resistance to the circuit formed by the RTD 819. The benefit of matching temperature sensors (e.g., diodes, RTD, thermistor) and/or the temperature sensor circuits is that calibrations between the sensors is minimized or eliminated and the temperature change between resistors is generally proportional to the change in differential resistance or differential current of the temperature sensor circuits, particularly over the measuring ranges of interest, e.g., approximately −50 degrees Celsius through +50 degrees Celsius.

The test sensor 800 is typically energized by connecting the test sensor 800 to a meter associated with a fluid analyte system. Such meters are described further below. The test sensor 800 can be inserted into a test sensor port, or dispensed from a test sensor port associated with the meter, such that meter contacts connect with the test-sensor contacts (e.g., 814a, 814b, 815) to allow current to flow through each temperature sensing element.

Figure 9:
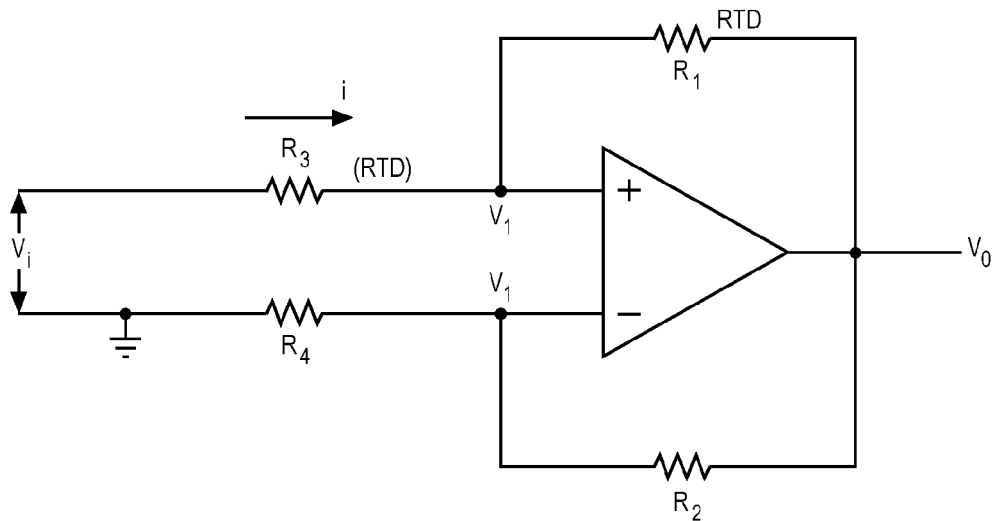
FIG. 9 illustrates a circuit diagram for determining differential temperatures according to another embodiment.
Figure 10:
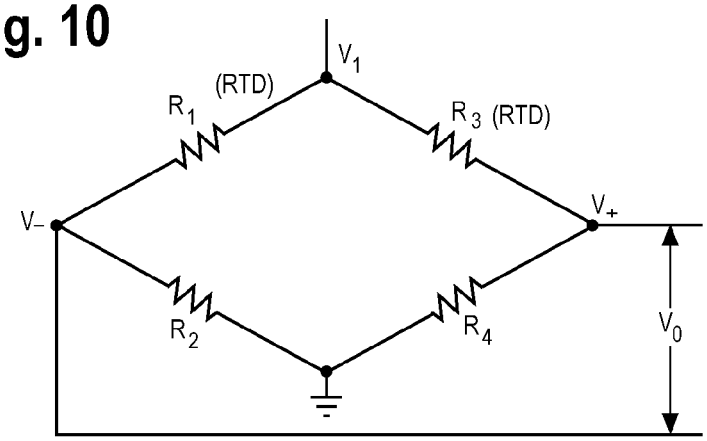
FIG. 10 illustrates a circuit diagram for determining differential temperatures according to another embodiment.
Figure 11:
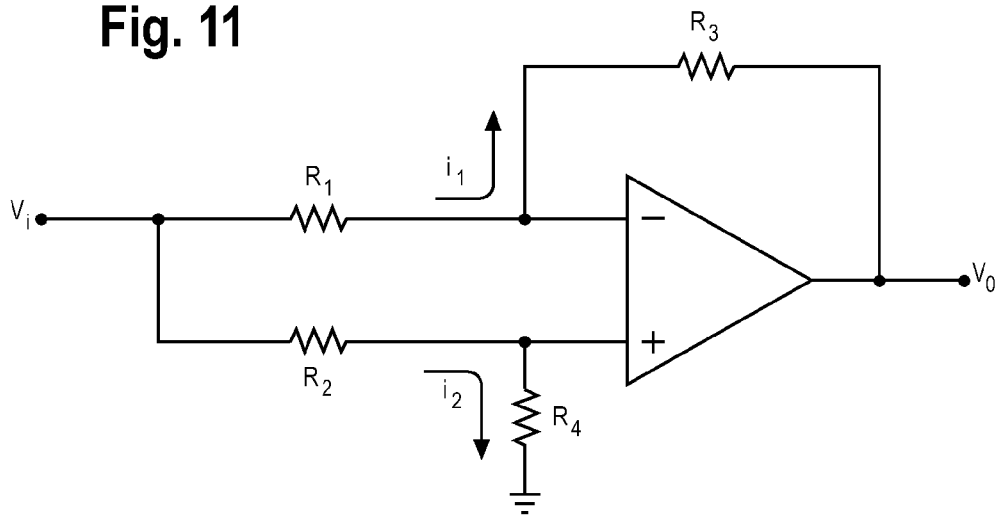
FIG. 11 illustrates a circuit diagram for determining differential temperatures according to another embodiment.

FIGS. 9-11 illustrate exemplary circuit diagrams for determining differential temperatures in test sensors. The circuit diagrams in FIGS. 9-11 include various configurations of an amplifier and resistors, R1, R2, R3, and R4, which may include two resistance temperature detectors. The components illustrated in the circuit diagrams may be disposed in various components of a fluid analyte system including on a test sensor and in a meter. For example, resistors R1 and R3 may be located on a test sensor similar to test sensors described above. An amplifier or other device for energizing the circuit along with resistors R2 and R4 may be disposed in a meter. It is contemplated that the non-temperature sensing resistors, such as R2 and R4 in FIGS. 9 and 10, can be matched in certain embodiments to tolerances approximately the same or tighter than R1 and R3 using methods known in the art. Furthermore, it is contemplated that the resistance of the non-temperature sensing resistors (e.g., R2 and R4) are equal or substantially equal, and that the resistance of the temperature sensing resistors (e.g., R1 and R3) are equal or substantially equal. In other words, it is desirable for the various resistor pairs to be matched. While resistors, R2 and R4, and resistors, R1 and R3, can be matched very closely, some mismatch can occur which can cause measurement errors in making resistance-based temperature measurements. Furthermore, reducing the mismatch can increase the cost of fabricating a test sensor with temperature sensing elements.

The error in measurement of the differential temperature can depend on a number of factors including the absolute temperature, T; the measured temperature difference, $\Delta T_m$; the real temperature difference, $\Delta T_r$; the temperature coefficient of resistance of the temperature sensing element, A (e.g., RTD, thermistor); the mismatch between R1 and R3, m; and the mismatch between $R_2$ and $R_4$, n. For the circuit diagram shown in FIG. 9, the error in the measurement of differential temperature can be determined using the following equation:

$$\text{error} = \Delta T_m - \Delta T_r = \frac{2(m-n)}{2+n}\left(\Delta T_r - \frac{1}{A} - T\right) + \frac{n}{n+2}\Delta T_r \quad \text{(Equation 1)}$$

where A is the temperature coefficient of resistance of R1 and R3;
R1 and R3 are approximately matched (i.e., minor mismatch); and
R2 and R4 are approximately matched (i.e., minor mismatch).

FIG. 10 illustrates a circuit diagram for determining differential temperatures according to another embodiment. It is contemplated that a differential temperature sensing arrangement with two RTD resistors, R1 and R3, in a bridge circuit also includes two additional resistors that are matched to approximately the same or tighter tolerances than R1 and R3 using methods known in the art. The error in the measurement of differential temperature for the circuit in FIG. 10 can be determined using the following equation:

$$\text{error} = \Delta T_m - \Delta T_r = \left(1 - \frac{m+1}{n+1}\right)\left(\frac{1}{A} + T - \Delta T_r\right) \quad \text{(Equation 2)}$$

where A is the temperature coefficient of resistance of R1 and R3;
R1 and R3 are approximately matched (i.e., minor mismatch); and
R2 and R4 are approximately matched (i.e., minor mismatch).

In embodiments where resistors R2 and R4 match very closely, n is approximately equal to zero, and then Equation 2 reduces to:

$$\text{error} = \Delta T_m - \Delta T_r \approx m\left(\Delta T_r - \frac{1}{A} + T\right) \quad \text{(Equation 3)}$$

Equation 3 can be used to assess various parameters in establishing a system for measuring differential temperatures with resistance-based temperature sensing elements. For example, as the mismatch between resistors, R1 and R3, increases, Equation 3 suggests that more error is introduced to the differential temperature measurement. The error in measuring differential temperature measurement can also increase for the combination of small real temperature differences, $\Delta T_r$, and high absolute temperatures, T, that lead to increased values for T minus $\Delta T_r$. Furthermore, an increase in the temperature coefficient of resistance, A, can lead to a decrease in error. It is contemplated that in certain embodiments, resistors R1 and R3 will include materials having a high temperature coefficient of resistance, A, and a low mismatch, m.

An illustration applying Equation 3 is made for the use of platinum materials in resistors, R1 and R3. The temperature coefficient of resistance for platinum is 0.0038. A typical range for absolute temperature and the real difference is approximately zero to 40 degrees Celsius. Thus, assuming for purposes of this illustration that an error of less than one degree Celsius is desired, the absolute value of the mismatch between R1 and R3 is preferably less than or equal to the absolute value of the temperature coefficient of resistance, A. So for platinum, the mismatch between R1 and R3 should be less than or equal to 0.38 percent for a differential temperature measurement error of less than one degree Celsius.

FIG. 11 illustrates a circuit diagram for determining differential temperatures according to another embodiment. A differential temperature sensing arrangement with two RTD resistors, R1 and R2, and two additional resistors, R3 and R4. The error in the measurement of differential temperature for the circuit in FIG. 11 can be determined using the following equation:

$$\text{error} = \Delta T_m - \Delta T_r = \frac{m-n}{1+n}\left(\Delta T_r - \frac{1}{A} - T_1\right) \quad \text{(Equation 4)}$$

where A is the temperature coefficient of resistance of R1 and R2;
R1 and R2 are approximately matched (i.e., minor mismatch);
R3 and R4 are approximately matched (i.e., minor mismatch); and
The resistance of R2 is much less than the resistance of R4.

In embodiments where resistors R3 and R4 match very closely, n is approximately equal to zero, and Equation 4 reduces, similar to Equation 3, to the following expression:

$$\text{error} = \Delta T_m - \Delta T_r \approx m\left(\Delta T_r - \frac{1}{A} + T\right) \quad \text{(Equation 5)}$$

The relationships illustrated in Equations 1-5 show that when the two normal resistors (i.e., the non-temperature sensing elements) are very closely matched, the exemplary test sensor arrangements lead to the same error in differential temperature measurement that is based on the mismatch between the temperature sensing elements in the circuit.

Temperature sensor configurations for applying differential temperature measurement techniques, such as those described in this application, can be particularly beneficial for disposable test sensors, and in general, for any type of test sensor associated with a temperature sensitive application. Non-limiting examples of test sensor applications can include test sensors for physical, mechanical, chemical, and biochemical applications. For example, the test sensors may be employed with the system described in FIGS. 1-2. In one non-limiting example, certain test sensors may be refrigerated or otherwise subject to cold temperature before use (e.g., HbA1C reagent, other in vitro diagnostic reagents). After removal from a cold source, such test sensors are generally allowed to equilibrate to the warmer ambient temperature. However, the actual temperature of the test sensor at testing may still be different from the temperature of the meter used to analyze a sample placed on the test sensor. In another non-limiting example, a test sensor and/or reagent may have been placed in a hot environment before use and the test sensor and/or reagent may be equilibrating to the cooler ambient temperature. The application of differential temperature measurements using differential temperature sensor(s) would allow the temperature difference(s) between the meter and the test sensor or reagent to be determined. It is also contemplated that determining accurate temperature values for the reagent and/or test sensor would be helpful for reagent calibration algorithms for temperature-sensitive diagnostic reagents—e.g., HbA1C, immune assays. For example, by having the ability to accurately assess fluctuations within a non-controlled environment (e.g., changing temperature), certain tests that are desirably performed in a well-controlled environment (e.g., certain immuno assays and/or immuno chemistry assays, which can be detected by electrochemical or optical techniques) can now be performed outside of the laboratory (e.g., in a sample provider's home, school, or work place).

Other non-limiting applications of differential temperature sensor(s) include test sensors that are body-insertable or implantable and include reusable electronics, such as a meter using disposable test sensors. A differential temperature sensor configuration utilizing both both reusable and disposal aspects of the system allows for the actual temperature of the test sensor to be determined along with the differential temperatures between a reagent, ambient temperature, and/or body temperature.

Differential temperature sensors provide an economical way to determine differential temperatures between a meter and a reagent, and also provide multiple useful applications such as increased accuracy in determining reagent temperature, toning of a reagent temperature indicator, minimizing human error while optimizing meter operations by allowing an auto-start capability in the meter once a desirable reagent temperature is reached, determining the readiness of the reagent for testing based on the reagent falling within a desirable temperature range, and/or reducing temperature-related errors during analyte concentration determinations of a fluid sample.

It is contemplated that in certain embodiments it may be desirable to assess temperature gradients on a housing or casing of a temperature-sensitive instrument, such as a fluid-analyte meter. Differential temperature sensors can provide a particularly useful application for assessing such gradients. For example, differential temperature sensors can be beneficial for determining the heat flux across the housing of a fluid analyte meter due to air flowing along the outside of the housing. Another benefit may be to detect if a heat source, such as a user's body part and/or some external electronics, are in contact with a temperature-sensitive portion of the meter. If configurations using multiple differential temperatures sensors, ambient temperature can be determined along with temperature differences between two objects on the meter contacting each other. It is further contemplated that differential temperature sensor may have desirable applications in fluid-analyte-monitoring systems worn by the user, such as patch pumps or continuous glucose-monitoring systems, particularly since differential temperature sensors provide an economical approach for correcting effects due to localized heat sources, such as randomized contact with the user's body.

It is contemplated that in certain embodiments, one or more differential temperature sensors are disposed on the housing or casing of a fluid-analyte meter that are connected via a connective cable or trace to a printed circuit board within the meter. The differential temperature sensor(s) may be based on thermocouple(s) and can be directly printed onto the casing of the meter. The connective cable or trace can provide a convenient connection to a processor located on the circuit board and allow efficient processing of differential temperature data and increased accuracy of fluid analyte concentration determinations.

In certain embodiments, differential temperature may be determined on a rechargeable battery associated with a fluid-analyte meter. For example, thermocouple-type configuration(s) could be printed onto the outer casing of a battery and monitored for changes in temperature. It is also contemplated that a differential temperature can be determined in any other location within a meter (e.g., on a printed circuit board within a meter).

Figure 12A:
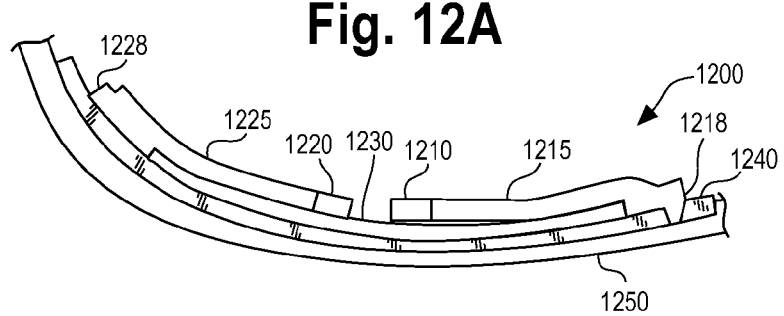
FIG. 12A illustrates a side view for a test sensor for determining differential temperatures using one or more thermocouples according to another embodiment.
Figure 12B:
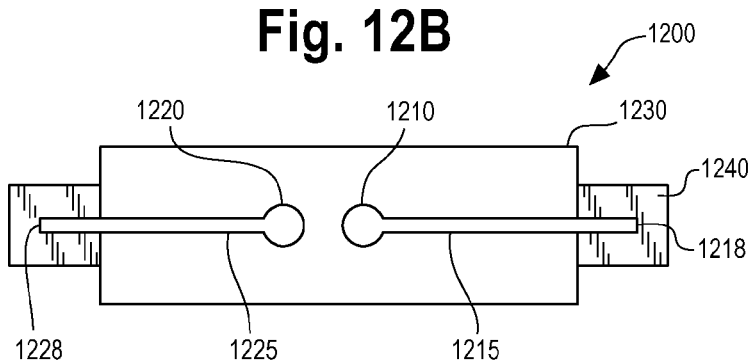
FIG. 12B illustrates a top view of the test sensor in FIG. 12A.

Turning now to FIGS. 12A-B and 13A-B, additional non-limiting embodiments are illustrated of differential temperature measuring devices configured for determining differential temperature(s) on a housing or other protective casing of a temperature-sensitive instrument, such as a blood glucose meter. FIGS. 12A-12B illustrate a temperature sensor 1200 for determining differential temperature using one or more thermocouples interface pairs. The sensor 1200 can be disposed on an outer casing 1250 of a temperature-sensitive instrument, such as a fluid-analyte meter. The temperature sensor includes a plurality of isothermal electrodes disposed on an insulative layer and conductive trace (s) that are at least partly disposed on an outer casing 1250. In certain embodiments, the temperature sensor 1200 includes a first isothermal electrode 1210 and a second isothermal electrode 1220 that are each connected via conductive traces that lead to thermocouple junctions—i.e., the temperature measuring points. A first temperature measurement point occurs at a first thermocouple junction 1218 where a first conductor material 1215 (e.g., conductive trace) and a second conductor material 1240 (e.g., conductive layer) come into contact with each other. A second temperature measurement point occurs at a second thermocouple junction 1228 where a third conductor material 1225 (e.g., (conductive trace) and the second conductor material 1240 come into contact with each other. In certain embodiments, an insulator layer 1230 may be disposed along at least a portion of the area between the first conductor material 1215 and the second conductor material 1240 so as to isolate the contact at the first thermocouple junction 1218. Similarly, the same or a different insulator material may be disposed between the third conductor material 1225 and the second conductor material 1240 so as to isolate the contact between the two elements to the second thermocouple junction 1228.

The first and second isothermal electrodes 1210, 1220 in the temperature sensor 1200 are the measuring or receiving points for electric signals generated at the first and second thermocouple junctions 1218, 1228. In certain embodiments, it may be desirable to place first and second isothermal electrodes 1210, 1220 as close to each other as possible without creating a pathway between the two electrodes. For example, the electrodes 1210, 1220 may be spaced approximately 0.5 mm apart. In another example, the spacing of the electrodes 1210, 1220 may range from about 0.3 mm to about 5 mm. It is also contemplated that in certain embodiments the first and second isothermal electrodes 1210, 1220 may be disposed farther away from each other and spatially closer to their respective first and second thermocouple junctions 1218, 1228, while still maintaining the first and third conductor materials 1215, 1225 and remaining isolated from the thermocouple junctions. Furthermore, it is contemplated that in certain embodiments the dimensions of the first and third conductor materials 1215, 1225 are approximately the same. The first and third conductor materials may also have the same or very similar physical and electrical properties. This can be beneficial because the determination of differential temperature can be further simplified if the physical and electrical properties of the combined first isothermal electrode 1210 and first conductor material 1215 and the combined second isothermal electrode 1220 and third conductor material 1225 are balanced or approximately minor each other. As discussed in the examples of FIGS. 5-11, such balancing or mirroring significantly simplifies the determination of differential temperature. As discussed above, an insulator material can be used to isolate the thermocouple junction where conductive materials are overlaying each other as shown in FIGS. 12A-B.

Figure 13A:
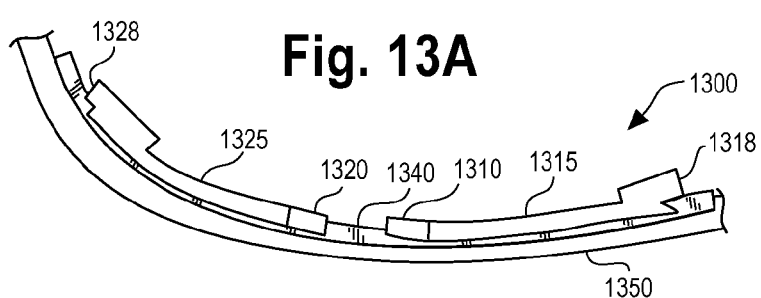
FIG. 13A illustrates a side view for a test sensor for determining differential temperatures on a casing of a meter using one or more thermocouples according to another embodiment.
Figure 13B:
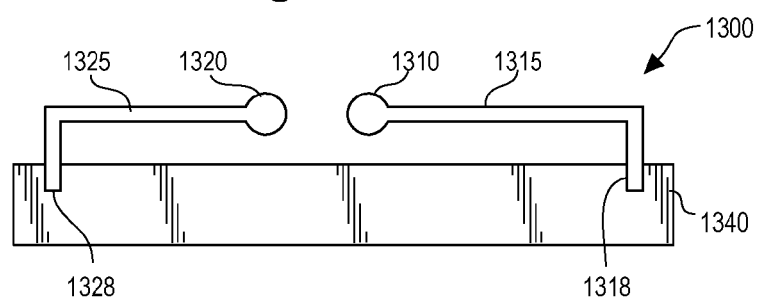
FIG. 13B illustrates a top view of the test sensor in FIG. 13A.

Turning now to FIGS. 13A-13B, in certain embodiments, a specific insulator layer may not be used, and instead the conductive materials may be offset from each other on an outer casing of a fluid analyte meter. The offset may result in the outer casing or some other material (e.g., spacer, air) serving a dual purpose, one of which is to isolate conductive materials to a specific junction. FIGS. 13A-13B illustrate a temperature sensor 1300 for determining differential temperature using one or more thermocouples interface pairs. Similar to the temperature sensor 1200 of FIGS. 12A-B, temperature sensor 1300 can also be disposed on an outer casing 1350 or on some other surface of a temperature-sensitive instrument, such as a fluid-analyte meter. The temperature sensor includes a plurality of electrodes disposed on or offset from the outer casing 1350 or other surface as shown in FIG. 13A. In certain embodiments, the temperature sensor 1300 includes a first electrode 1310 and a second electrode 1320 that are each connected via conductive traces that lead to thermocouple junctions—i.e., the temperature measuring points. A first temperature measurement point occurs at a first thermocouple junction 1318 where a first conductor material 1315 (e.g., conductive trace) and a second conductor material 1340 (e.g., conductive layer) come into contact with each other. A second temperature measurement point occurs at a second thermocouple junction 1328 where a third conductor material 1325 (e.g., conductive trace) and the second conductor material 1340 come into contact with each other. In certain embodiments, the first conductor material 1315 and the second conductor material 1340 are isolated (i.e., not in conductive contact with each) except at the first thermocouple junction 1318. Similarly, the conductive contact between the third conductor material 1325 and the second conductor material 1340 so as to isolate or limit the contact between the two elements to the second thermocouple junction 1328.

The first and second electrodes 1310, 1320 in the temperature sensor 1300 are the measuring or receiving points for electric signals generated at the first and second thermocouple junctions 1318, 1328. Electrodes 1310, 1320 can be configured to be isothermal, but are more likely to exhibit isothermal-like or quasi-isothermal properties, rather than true isothermal properties. This is due to minor variances during the manufacturing of the temperature sensor 1300. In certain embodiments, it may be desirable to place first and second electrodes 1310, 1320 as close to each other a possible without creating a pathway between the two electrodes. For example, the electrodes 1310, 1320 may be spaced approximately 0.5 mm apart. In another example, the spacing of the electrodes 1310, 1320 may range from about 0.3 mm to about 5 mm. It is also contemplated that in certain embodiments the first and second electrodes 1310, 1320 may be disposed farther away from each other and spatially closer to their respective first and second thermocouple junctions 1318, 1328. Furthermore, it is contemplated that in certain embodiments the dimensions of the first and third conductor materials 1315, 1325 are approximately the same. The first and third conductor materials may also have the same or very similar physical and electrical properties. This can be beneficial because the determination of differential temperature can be further simplified if the physical and electrical properties of the combined first electrode 1310 and first conductor material 1315 and the combined second electrode 1320 and third conductor material 1325 are balanced or approximately minor each other. As discussed in the examples of FIGS. 5-12, such balancing or mirroring significantly simplifies the determination of differential temperature.

In certain embodiments, the first and second electrodes 1310, 1320 and the first conductor and third conductor materials 1315, 1325 are offset from the second conductor material 1340. The offset can vary and can include offsetting the first and third conductor materials 1315, 1325 to be approximately parallel to the second conductor material 1340. As discussed previously, the first and second electrodes 1310, 1320 and the first and third conductor materials 1315, 1325 may be printed onto the interior of the outer protective casing of a fluid-analyte meter or onto a layer attached to the outer protective casing.

For isothermal or quasi-isothermal differential temperature sensors on an outer casing of a fluid-analyte meter, such as those illustrated in FIGS. 12 and 13, the differential temperature can be determined between the first thermocouple junction 1218, 1318 and the second thermocouple junction 1228, 1328. It is also contemplated that in certain embodiments, differential temperature can be determined between the first electrodes 1210, 1310 and their respective first thermocouple junctions 1218, 1318 where different conductive materials, such as those described herein for related thermocouple applications, are used for the first electrodes 1210, 1310 and the first conductor materials 1215, 1315. Similarly, the differential temperature between the second electrodes 1220, 1320 and their respective second thermocouple junctions 1228, 1328 can be determined, as well, where different conductive materials are used for the second electrodes 1215, 1315 and the conductor materials 1225, 1325.

It is further contemplated that several hot junctions (e.g., thermocouple interfaces or junctions) can be formed in a series for temperature sensors 1200, 1300. By using different materials for the conductor materials or traces, thermocouples can be formed at the intersection of the different conductive materials. The formation of the thermocouple junctions allow the determination of differential temperatures between the different thermocouple interfaces based on thermoelectric principles. The electrical signals generated at the electrodes by the thermocouple junctions correlate to the differential temperature. That is, the change in voltage across the thermocouple in temperature sensor(s) 1200, 1300 may be proportional to the change in temperature (e.g., differential temperature) between the first thermocouple junctions 1218, 1318 and their respective second thermocouple junction(s) 1228, 1328. In one embodiment, the output electrical signal through the electrode(s) 1210, 1220, 1310, 1320 can be approximately a few microvolts per degree Celsius differential temperature.

As discussed earlier, the electrical signals generated by the thermocouples correlate to the differential temperature between interface pairs. It is contemplated that in certain embodiments that the thermocouple interfaces are configured to be isothermal or quasi-isothermal, such as the configurations illustrated in FIGS. 12A-B and 13A-B. It is further contemplated more a fewer thermocouple interface pairs can be fabricated into a temperature sensor on a meter casing as they are needed to meet a desired sensitivity in temperature measurements.

The conductive materials used in the embodiments described herein can be fabricated from carbon materials such as carbon paste, carbon fibers, or carbon inks. In certain embodiments, semiconductor-type materials may be used. In further embodiments, different grades of the same materials may be us, as well. The conductive materials can also be fabricated using gold, platinum, palladium, gold, or similar metallic materials. In certain embodiments, the conductive materials can be screen printed with conductive inks, ink-jet printed using dissimilar conductive inks, pad printed, rollercoated, laminated, non-contact printed, or otherwise disposed onto the test sensor substrate, the meter casing, the insulator layer, or another conductor material. It is also contemplated that thin-film processes such as laser techniques (e.g., laser deposition, laser ablation) or light-activated conductive polymers can be used, as well in the formation of the conductive trace. The insulator material, substrate, and/or meter casing may comprise polycarbonate, polyethylene terephthalate, other insulating polymer materials, green tape, ceramic materials, amorphous silicates, or other insulator-type materials. In certain embodiments, the conductivity difference between the conductor materials and any insulator materials or the casing are different by at least two orders of magnitude.

Figure 14A:
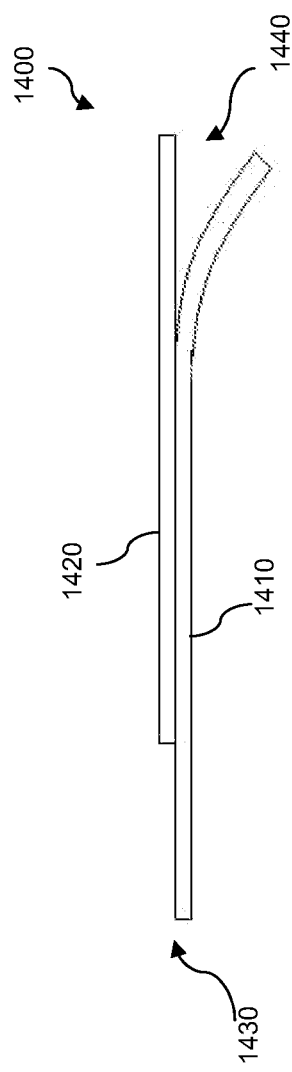
FIG. 14A illustrates a side view for a test sensor for determining differential temperatures according to another embodiment.
Figure 14B:
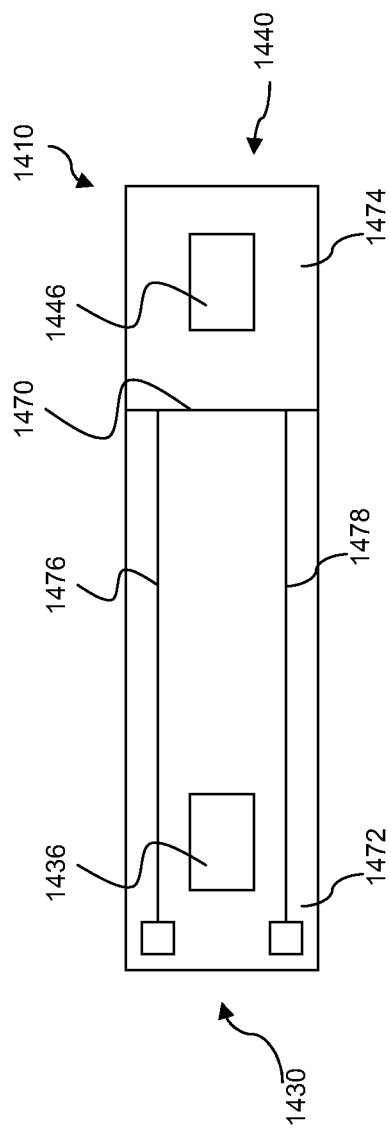
FIG. 14B illustrates a top view of a base for the test sensor in FIG. 14A.

Referring now to FIGS. 14A-16B, non-limiting embodiments are illustrated for test sensors including a feature for improved acquisition of ambient temperature. FIGS. 14A, 14B illustrates a test sensor 1400 including a base 1410 and a lid 1420. The test sensor 1400 also includes a connection end 1430 where the test sensor 1400 interfaces with a meter, and a fluid-receiving end 1440 where the test sensor 1400 receives a fluid sample. A first temperature sensing element 1446 is positioned at or in close proximity to the fluid-receiving end 1440. A second temperature sensing element 1436 is positioned at or in close proximity to the connection end 1430 of the test sensor 1400. The temperature sensing elements 1436, 1446 can include a thermocouple, a thermopile, a RTD, a diode device or combinations thereof as described herein. As previously described, a differential temperature reading can be collected from the first temperature sensing element 1446 and the second temperature sensing element 1436. The test sensor 1400 can further include any additional components and/or features for collecting and electrochemically or optically analyzing a fluid sample (e.g., a reagent, a capillary channel, a vent, a light detector, etc.).

The base 1410 of the test sensor 1400 includes a break junction 1470 located between a first portion 1472 of the base 1410 and a second portion 1474 of the base 1410. At least the second portion 1474 of the base 1410 is made from a semi-rigid or a flexible material. This may be a polymeric material, such as a low softening point thermoplastic (e.g., low density polyethylene. It is contemplated that other materials may be used. The break junction 1470 is electrically coupled to a first electrical lead 1476 and a second electrical lead 1478. When the test sensor 1400 is inserted into a meter, an electrical pulse is transmitted from the meter to the break junction 1470 via the first electrical lead 1476 and the second electrical lead 1478. When the electrical pulse is received by the break junction 1470, the bond between the second portion 1474 and the lid 1420 is broken. For example, the electrical pulse can cause sufficient resistive heating at the break junction 1470 to weaken and/or break the bond between the second portion 1474 and the lid 1420. As a result, the second portion 1474 releases and extends away from the lid 1420, for example, as a flap. Because the second portion 1474 includes the first temperature sensing element 1446, the first temperature sensing element 1446 is suspended in the ambient environment, advantageously providing for improved measurements of ambient temperature by the first temperature sensing element 1446.

According to the alternative embodiment illustrated in FIGS. 15A-B, a test sensor 1500 includes a base 1510, a lid 1520, a connection end 1530, a fluid-receiving end 1540, a first temperature sensing element 1546, a second temperature sensing element 1536, a break junction 1570, a first portion 1572 of the base 1510, a second portion 1574 of the base 1570, and first and second electrical leads 1576, 1578, respectively. When the test sensor 1500 is inserted in a meter, an electrical pulse is transmitted to the break junction 1570 via the electrical leads 1576, 1578. The electrical pulse causes the bond between the second portion 1574 and the lid 1520 to break (e.g., via resistive heating) along the illustrated dashed line, releasing the second portion 1574 as a flap extending from the lid 1520. Accordingly, it is contemplated that the second portion 1574 can be configured in various shapes and/or sizes.

According to the alternative embodiment illustrated in FIGS. 16A-16B, a test sensor 1600 includes a base 1610, a lid 1620, a connection end 1630, and a fluid-receiving end 1640. The test sensor 1600 differs from the test sensor 1400 and the test sensor 1500 in that the lid 1620 includes a break junction 1670 instead of the base 1610. Accordingly, the lid 1620 also includes a first portion 1672, a second portion 1674, a first electrical lead 1676, and a second electrical lead 1678. When the test sensor 1600 is inserted in a meter, an electrical pulse is transmitted to the break junction 1670 via the electrical leads 1676, 1678. The electrical pulse causes the bond between the second portion 1674 and the base 1610 to break, releasing the second portion 1674 as a flap extending from the base 1610. Accordingly, a first temperature sensing element 1646 on the base 1610 is advantageously exposed to the ambient environment.

The illustrated and described test sensors 1400, 1500, 1600 are non-limiting examples of embodiments for forming flaps on a test sensor to enhance measurement of ambient temperature. It is contemplated that a spacer can optionally be included in the test sensors between the base and the lid. Additionally, it is contemplated that the first and/or second temperature sensing elements can be included on and/or in any of the test sensor layers (i.e., the base, the spacer, and/or the lid) in alternative embodiments. If the first temperature sensing element is located within a layer, the break junction can be configured within that layer to release a portion of the thickness of the layer and expose the first temperature sensing element to the ambient environment. Still further the breaking of the bond between the second portion and the adjacent layer(s) (or a portion of the thickness of a layer) can be achieved by mechanical components instead of the electrical components (e.g., the first and second electrical leads causing resistive heating at or adjacent to the break junction) described above.

It is also contemplated that the second temperature sensing element illustrated and described above can be located internally within a meter instead of on the test sensor. Indeed, the ambient temperature can be acquired either in reference to the internal temperature of a meter or by other means.

Figure 2:
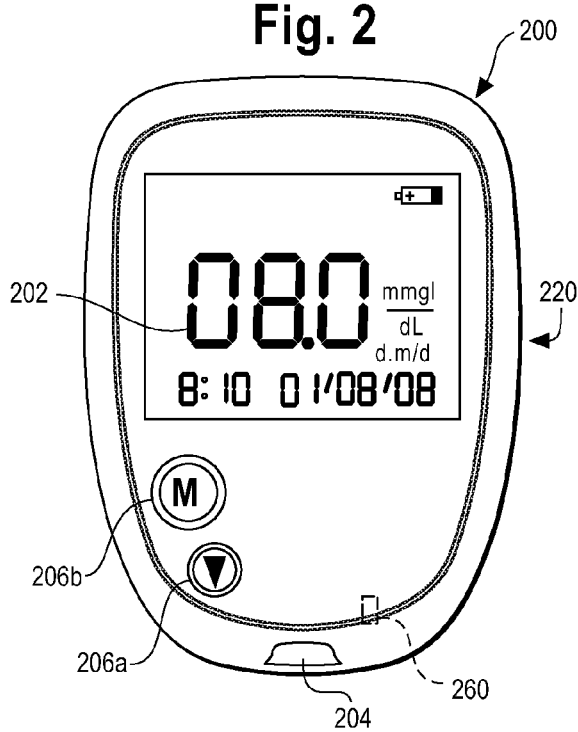
FIG. 2 illustrates a portable meter with a display according to another embodiment.

Turning now to FIGS. 17A-F, several non-limiting embodiments are illustrated for the thin-film or strip-type test sensors 1700 including thermocouples to measure differential temperature in a fluid analyte system, such as the non-limiting systems described in the embodiments of FIGS. 1-2. In particular, FIGS. 17A-E illustrate alternative embodiments for a base 1710 of a test sensor 1700 illustrated in FIG. 17F, which are further alternative embodiments to the base 510 of the test sensor 500 illustrated in and described for FIGS. 5A-B.

The test sensor 1700 includes at least a base 1710 and a lid 1720. The test sensor 1700 can optionally include a spacer (not shown) between the base 1710 and the lid 1720. The test sensor 1700 further includes a connecter end 1730, a fluid-receiving end 1740, a capillary channel 1721 (e.g., after the lid 1720 is placed over the base 1710), and a testing or reagent area 1723 as previously described.

The base 1710 includes a counter electrode 1718a, a working electrode 1718b, a first conductive trace 1716a, a second conductive trace 1716b, and a third conductive trace 1716c, which are electrically isolated except at a reference junction 1715 formed between the first conductive trace 1716a and the third conductive trace 1716c, and at a hot junction 1719 formed between the second conductive trace 1716b and the third conductive trace 1716c. By using a material for the third conductive trace 1716c that is different than the conductive material used for the first and second conductive traces 1716a, 1716b, a thermocouple is formed at the reference junction 1715 and a thermocouple is formed at the hot junction 1719 that allow for the determination of the differential temperature between junctions 1715, 1719 based on thermoelectric principles (e.g., the Seebeck effect). According to one embodiment, the first and second conductive traces 1716a, 1716b are made of a noble metal (e.g., platinum, palladium, gold) and the third conductive trace 1719c is made of a carbon-based material (e.g., graphite). In an alternative embodiment, the first and second conductive traces 1716a, 1716b can be made of a carbon-based material and the third conductive trace 1716c can be made of a noble metal.

In the embodiments illustrated in FIGS. 17A-D, prior to forming the third conductive trace 1716c, at least the first and second conductive traces 1716a, 1716b are formed on the base 1710. A section 1727 (shown in hatching) of the first and/or second conductive traces 1716a, 1716b is then removed (e.g., via laser ablation or the like) from the base 1710. The third conductive trace 1716c is then formed over a portion of the section 1727, a portion of the first conductive trace 1716a, and a portion of the second conductive trace 1716b. Accordingly, in the embodiments illustrated in FIGS. 17A-D, the section 1727 assists in electrically isolating a portion of third conductive trace 1716c from the counter electrode 1718a, the working electrode 1718b, the first conductive trace 1716a, and/or the second conductive trace 1716b.

According to other embodiments, the third conductive trace 1716c can be electrically isolated without removing a section of the first conductive trace 1716a and/or the second conductive trace 1716b. For example, insulating materials can be used to electrically isolate a third conductive trace. As another non-limiting example, in FIG. 17E, the third conductive trace 1716c is electrically isolated from the second conductive trace 1716b by forming discontinuities 1725 (e.g., via laser ablation) in the second conductive trace 1716b.

Figure 17A:
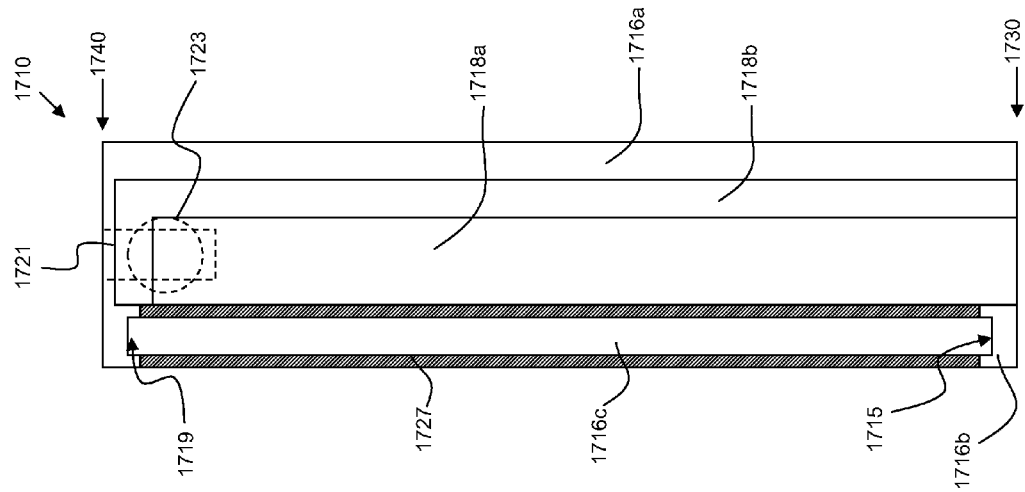
Figure 17B:
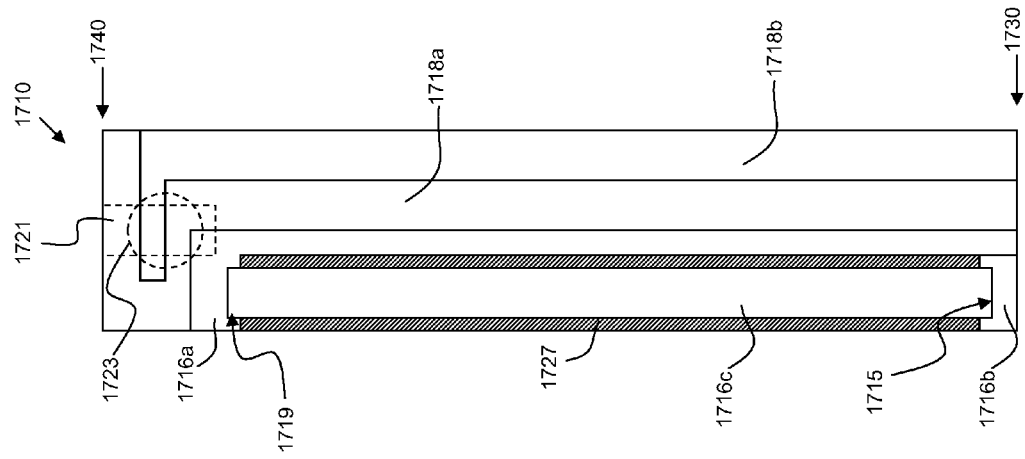
Figure 17C:
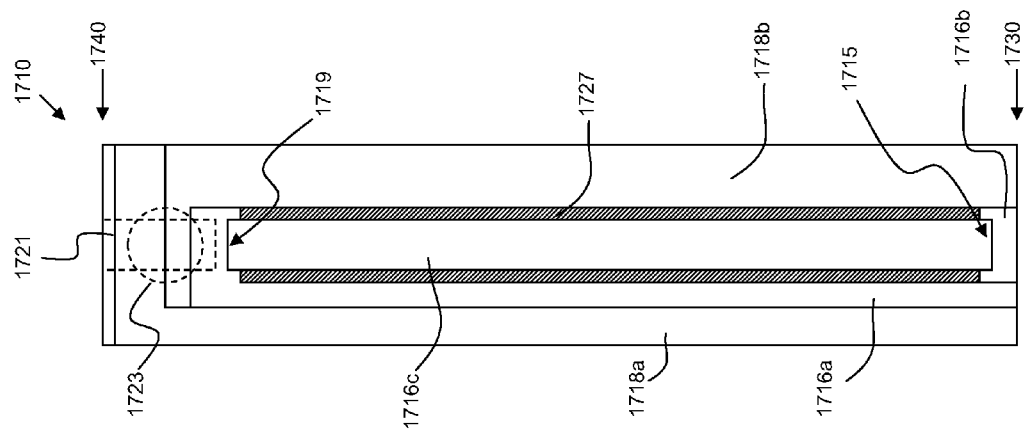

The hot junction 1719 and the reference junction 1715 can be located at various positions in the test sensor 1700. For example, in FIG. 17A and FIG. 17E, the hot junction 1719 is located directly below the reagent area 1723. In FIG. 17B, the hot junction 1719 is located below and lateral to the reagent area 1723. In FIG. 17C, the hot junction 1719 is located lateral to the reagent area 1723. And, in FIG. 17D, the hot junction 1719 is located at the reagent area 1723. It is contemplated that the hot junction 1719 and/or reference junction 1715 can also be formed at other locations than those illustrated.

While the test sensors illustrated in and described for FIGS. 17A-E include a counter electrode and a working electrode, it is contemplated that one or more additional electrodes (e.g., a trigger electrode, a hematocrit electrode, etc.) can be provided.

Additionally, it is contemplated that the thermocouple(s) can be located on the lid instead of the base of a test sensor. For example, FIGS. 18A-D illustrate a non-limiting embodiment of a test sensor 1800 that includes two thermocouples located on a lid 1820 of the test sensor 1800. The test sensor 1800 includes a base 1810, the lid 1820, and a spacer 1822 located between the base 1810 and the lid 1820. The base 1810 includes a counter electrode 1818a and a working electrode 1818b. The lid 1820 includes a first conductive trace 1816a, a second conductive trace 1816b, and a third conductive trace 1816c, which are electrically isolated, except at a reference junction 1815 formed between the first conductive trace 1816a and the third conductive trace 1816c, and at a hot junction 1819 formed between the second conductive trace 1816b and the third conductive trace 1816c. The electrical isolation can be achieved, for example, via insulating materials, an ablation region 1827, and/or combinations thereof as previously described.

By using a material for the third conductive trace 1816c (e.g., a carbon-based material) that is different than the conductive material used for the first and second conductive traces 1816a, 1816b (e.g., a noble metal), a thermocouple is formed at the reference junction 1815 and a thermocouple is formed at the hot junction 1819 that assist in determining the differential temperature between junctions 1815, 1819 based on thermoelectric principles (e.g., the Seebeck effect).

When the lid 1820, the spacer 1822 and the base 1820 are assembled, a capillary channel 1821 is formed that is adapted to receive fluid for testing at a fluid-receiving end 1840. The capillary channel extends from the fluid-receiving end 1840 towards a connection end 1830, which is adapted to couple to a meter as previously described. When the fluid-receiving end 1840 of the sensor 1800 is placed into a sample fluid (e.g., blood), a portion of the sample fluid is drawn into the capillary channel 1821 by capillary action. The fluid then chemically reacts with the reagent material (not shown) in the test sensor 1800 so that a signal indicative of the analyte (e.g., glucose) concentration in the sample fluid being tested is supplied and subsequently transmitted to an electrical assembly.

Advantageously, the test sensor 1800 can also measure AC characteristics of the sample fluid (e.g., capacitance values). FIG. 18D illustrates a sectional view generally along a longitudinal axis of the test sensor 1800. As seen in FIG. 18D, when the lid 1820, the spacer 1822, and the base 1810 are assembled, the third conductive trace 1816*c* is disposed above and spaced apart from the counter electrode 1818*a* and the working electrode 1818*b* in the capillary channel 1821. Accordingly, when a sample fluid fills the capillary channel 1821, the sample fluid can act as a dielectric between the third conductive trace 1816*c* and the electrodes 1818*a*, 1818*b* to achieve one or more capacitors.

FIG. 18E illustrates the equivalent circuit that is formed by the conductive trace 1816*c* and the electrodes 1818*a*, 1818*b* when a fluid sample fills the capillary channel 1821. As shown in FIG. 18E, a first capacitor C1 is formed between the working electrode 1818*b* and the third conductive trace 1816*c* and a second capacitor C2 is formed between the counter electrode 1818*a* and the third conductive trace 1816*c*. In the illustrated embodiment, the capacitors C1 and C2 are connected in series. According to one non-limiting embodiment, the separation distance between the third conductive trace 1816*c* and the electrodes 1818*a*, 1818*b* can be, for example, approximately 125 micrometers. In some embodiments, the separation distance can be between approximately 75 micrometers and approximately 250 micrometers.

The measured capacitance at the capacitor C1 and/or the capacitor C2 depends upon the properties of the dielectric medium (i.e., the sample fluid). For example, the measured capacitance of blood will vary depending upon the hematocrit concentration in the blood. Accordingly, locating the thermocouple(s) on the lid and the electrodes on the base allows for direct and independent measurements of temperature, analyte concentration, and/or hematocrit concentration in the same sample fluid.

It is contemplated that, according to alternative embodiments, the thermocouple(s) can be located on the base and the electrodes can be located on the lid to form the capacitor(s) in the capillary channel. Alternatively, one of the counter electrode or the working electrode can be located on the base, and the other electrode can be located on the lid along with a conductive trace to form a thermocouple between the conductive trace and the electrode on the lid and a capacitor between the conductive trace and the electrode on the base. Similarly, one of the counter electrode or the working electrode can be located on the lid, and the other electrode can be located on the base along with a conductive trace to form a thermocouple between the conductive trace and the electrode on the base and a capacitor between the conductive trace and the electrode on the lid.

Aspects of the present invention are not limited to using the temperature sensing techniques described above. For example, some embodiments may measure infrared (IR) radiation to determine the reference temperature (at the cold junction). In general, all materials at temperatures above absolute zero continuously emit energy. Infrared radiation is part of the electromagnetic spectrum and occupies frequencies between visible light and radio waves. The infrared part of the spectrum spans wavelengths from about 0.7 micrometers to about 1000 micrometers. The wave band usually used for temperature measurement is from about 0.7 to about 20 micrometers. Accordingly, aspects of the present invention may employ a thermopile sensor that measures the test sensor temperature by detecting blackbody radiation emitted from the test sensor or other object. By knowing the amount of infrared energy emitted by an object and its emissivity, the temperature of the object can be determined. In particular, the thermopile sensor may generate a voltage proportional to incident infrared radiation. Because the temperature of a surface of the object is related to the incident infrared radiation, the temperature of the surface can be determined from the thermopile sensor.

Alternatively, other embodiments employ an optical-sensing system. Temperature, for example may be determined by measuring light reflected from a thermochromic material. For example, the test sensor may include a thermochromic material, which indicates the temperature of the test sensor. The optical-sensing system includes a light source and a light detector. The light source directs photons at the thermochromic material and the light detector collects reflected photons to determine the temperature of the object.

The use of a thermopile sensor or an optical-sensing system to measure the temperature of an object is further described in U.S. patent application Ser. No. 12/252,348 titled "Method and Assembly for Determining the Temperature of a Test Sensor" and filed May 2, 2009, the contents of which are incorporated entirely herein by reference. In addition, techniques for diagnostically testing and calibrating a system employing a thermopile sensor or an optical-sensing system are described in U.S. patent application Ser. No. 12/796,324 titled "Method and Assembly for Determining the Temperature of a Test Sensor" and filed Jun. 8, 2010, the contents of which are incorporated entirely herein by reference.

Various processes may be implemented to apply a conductive trace to a test sensor. As described above, the conductive trace forms the connection between the hot junction (reagent end) and cold junction (meter end) of the test sensor. These processes, for example, may apply carbon, gold, palladium and/or other materials with thermoelectric properties to form the conductive trace. Alternatively, the conductive trace may be formed by clearing the metalized layer underneath the conductive trace, e.g., by using an Excimer laser.

In one exemplary process, the conductive trace is applied to the test sensor base/electrode material, which acts as the substrate. The conductive trace is registered to the electrode pattern and cured. This process may be performed on an offline, standalone station. The resulting pieces from this station can then be delivered to a primary production line to complete the manufacture of the test sensors.

In another exemplary process, a plastic material, such as polyethylene terephthalate (PET), is coated with a conductive material using screen printing and then cured. Alternatively, the plastic material mat be metalized. The plastic material may be coated in an offline, standalone station. The primary production line is configured to apply thin strips of the coated plastic to the test sensor base/electrode layer. The thin strips, in one embodiment, are applied with the conductive coating face down against the test sensor base/electrode layer. After application of the thin strips, manufacture of the test sensors may be completed on the primary production line. Subsequent processing may include the adding the reagent and forming the capillary channel by adding spacers and a lid to the base.

Yet another exemplary process employs a plastic material coated with a conductive material via screen printing. Unlike the process above, however, the conductive trace is applied to the other side of the test sensor base/electrode material. Because the electrode material and the conductive trace are on opposite sides of the test sensor, electrical contacts must be disposed on both sides of the test sensor to permit connection with the electrode material and the conductive trace. Accordingly, the meter receiving the test sensor must include a connector that connects with the electrical contacts on both sides of the test sensor, i.e., a two-sided connector.

Other processes for applying a conductive trace may include:
1. Dispensing one or more different carbon (or other conductive material) dots across an ablated gold junction to form the conductive trace.
2. Dispensing carbon, silver, or aluminum conductors that overlap to form different types of junctions.
3. Applying two layers, such as titanium/gold or $La_2Zr_2O_7$ (LZO)/gold, to the test sensor construction; ablating once to form the electrode circuit; and ablating a second time to remove only the top layer at specific junctions to produce a carbon/gold junction and a carbon/(titanium or LZO) junction.
4. Rollercoating a carbon layer on a continuous process and laser cutting or ablating the dried carbon layer to form the conductive trace.

Furthermore, the materials employed to the form a conductive trace may be modified to enhance the signal-to-noise ratio to improve the accuracy of measurements via the conductive trace. For example, where carbon is screen printed onto gold to form a thermocouple, the output is approximately 5-7 μV/° C. Adding material to the carbon can increase the output and provide a higher signal-to-noise ratio. One such material may be Perovakite, which exhibits high thermopower. In general, the output of a thermocouple depends on the material forming the thermocouple, so the use of semiconductors or other similar materials may improve the thermoelectric effect.

Additional considerations for the implementation of the embodiments described herein have been further identified. In particular, calculations of the reagent temperature $T_R$ at the temperature transitions (transient changes in temperature) are calculated according to meter temperature $T_m$ and the test sensor voltage measurement V taken by the meter. Meter temperature $T_m$ is the temperature measured by a temperature sensing measurement in the meter, while test sensor voltage measurement V is a measurement of the temperature differential in accordance with aspects of the present invention. An error deviation in the estimates may occur due to a time delay between the measurements of $T_m$ and V. The time delay occurs, for example, when the meter temperature $T_m$ is measured at a point, e.g., by a thermistor, outside a connector that receives the test sensor in the meter. Because the cold junction of the test sensor is disposed within the connector, the measurement of the meter temperature $T_m$ outside the connector is removed from the cold junction. The connector acts as a damper between the measurement point in the meter and the cold junction. It is therefore advantageous to measure the meter temperature $T_m$ within the connector and as close to the cold junction as possible. Measuring the meter temperature $T_m$ as close as physically possible to the cold junction significantly reduces the time delay and the estimate for the reagent temperature $T_R$ based on $T_m$ and V at the temperature transitions becomes more accurate.

Figure 19:
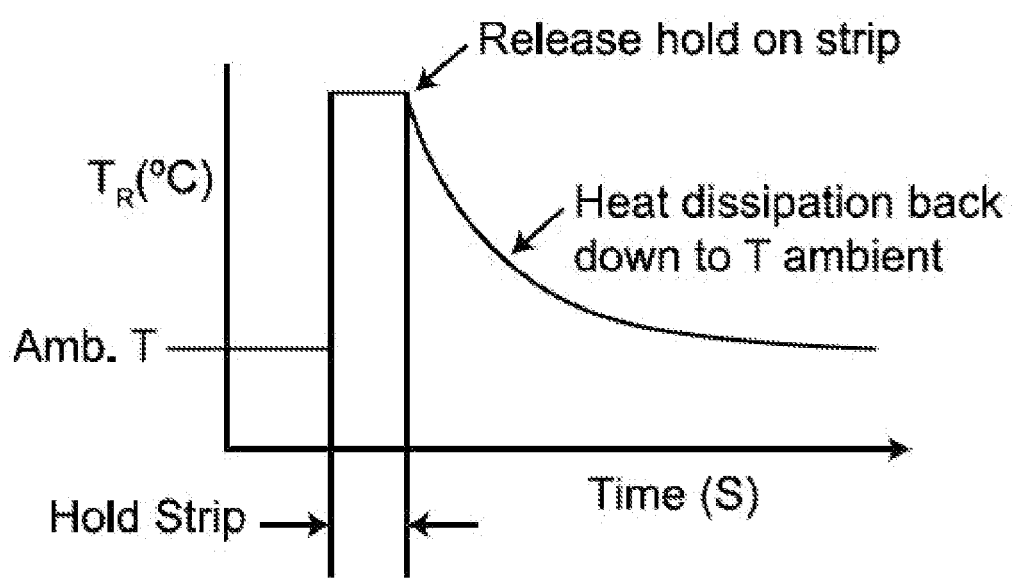
FIG. 19 illustrates a graph of the estimated reagent temperature as a function of time when handling of the test sensor transfers body heat to the test sensor.

In addition, it has also been determined that the measurement of reagent temperature $T_R$ based on $T_m$ and V are able to follow rapid heat transfer to and from the test sensor. For example, FIG. 19 illustrates $T_R$ as a function of time t when a user handles the test sensor in the area of the reagent and then releases the test sensor. The measurement of the reagent temperature $T_R$ starts at the ambient temperature but increases to a value greater than the actual ambient temperature when the user handles the test sensor and body heat is transferred to the test sensor. Once the user releases the test sensor, the heat from the user dissipates and $T_R$ approaches the actual ambient temperature again. Considering the effect of rapid heat transfer on the calculation of $T_R$ based on $T_m$ and V, it may be advantageous to wait until the heat effects from user handling have dissipated before $T_R$ is calculated to adjust the analyte concentration measured with the reagent. Accordingly, the meter may be programmed to wait until some point after the user has released the test strip before prompting the user to start analyte testing. In addition, a direct physical connection between meter and the cold junction may be employed to allow the test sensor to equilibrate with the meter temperature more quickly.

Although structures and techniques described herein may be employed to provide more accurate analyte concentration measurements, such structures and techniques may be employed in other advantageous applications. For example, the conductive trace may be employed to detect when a sample has been received by the test sensor. In particular, the test sensor experiences a sudden change in temperature when it receives a sample, such as a blood sample. Detection of this sudden change indicates that a sample is being received into the capillary channel.

In addition, a conductive trace may be employed to detect whether an appropriate volume of sample has been received by the test sensor, i.e., underfill detection. The conductive trace may be employed in addition to conventional underfill detection technique, an electrode, which are generally employed closer to the entrance of the capillary channel. For example, an electrode may be positioned to determine the trailing edge of the sample in the capillary, while the conductive trace is advantageously disposed upstream, e.g., near the reagent, to detect the leading edge of the sample in the capillary channel. Detection of the trailing and leading edges of the sample indicates whether the capillary is completely filled with the sample.

Turning now more generally to FIG. 1, a fluid analyte system 100 is illustrated including a meter 110 with a port for receiving and analyzing a fluid sample on a test sensor 120. The test sensor includes a connection end 130 where the test sensor 120 interfaces with the meter 110. The interface between the meter 110 and the test sensor 120 can allow the meter 110 to energize the test sensor 120 by applying, for example, a voltage difference across contacts on the test sensor and the meter. The test sensor 120 also includes a fluid-receiving end 140 for receiving a fluid sample into a fluid-receiving area 143 for subsequent analysis using the meter 110. A first temperature sensing element 146 is positioned in or in close proximity to the fluid-receiving area 143 of the test sensor 120. A second temperature sensing element 136 is positioned at the connection end 130 of the test sensor 120. With the test sensor 120 fully interfaced with the meter 110, the second temperature sensing element 136 may be disposed within or near the meter 110.

The test sensor 120 is typically provided with a capillary channel that extends from the fluid-receiving end 140 of the test sensor 120 to reagent material disposed in the fluid-receiving area 143. When the fluid-receiving end 140 is placed into fluid (for example, blood that is accumulated on a person's finger after the finger has been pricked), a portion of the fluid is drawn into the capillary channel by capillary action. The fluid then chemically reacts with the reagent material so that a signal indicative of the analyte (for example, glucose) concentration in the fluid being tested is supplied and subsequently transmitted to an electrical assembly as described further below. It is contemplated that the test sensors illustrated herein can have various dimensional configurations. For example, in certain embodiments dimensions of the test sensor can include widths ranging from approximately 3 millimeters to 10 millimeters, lengths ranging from 15 millimeters to 50 millimeters, and thicknesses ranging from 0.25 to 1.5 millimeters.

Analytes that may be determined using the device include glucose, lipid profiles (for example, cholesterol, triglycerides, LDL and HDL), microalbumin, hemoglobin $A1_C$, fructose, lactate, or bilirubin. The present invention is not limited, however, to devices for determining these specific analytes, and it is contemplated that other analyte concentrations may be determined. The analytes may be in, for example, a whole blood sample, a blood serum sample, a blood plasma sample, or other body fluids like ISF (interstitial fluid) and urine.

In FIG. 1, the meter 110 receives and engages the test sensor 120. The meter 110 measures the concentration of analyte for the sample collected by the test sensor 120. The meter 110 can include contacts for the electrodes to detect the electrochemical reaction of an electrochemical test sensor. Alternatively, the meter 110 can include an optical detector to detect the degree of light alteration for an optical test sensor. To calculate the actual concentration of analyte from the electrochemical reaction measured by the meter 110 and to generally control the procedure for testing the sample, the meter 110 employs at least one processor 112, which may execute programmed instructions according to a measurement algorithm. Data processed by the processor 112 can be stored in a memory 114. The meter 110 may also use the same or a different processor for various operations, such as, for example, power management or temperature functions, including executing routines for temperature prediction of ambient temperature. Furthermore, the meter can include a user interface.

The temperature sensing elements 136, 146 can operate as differential temperature sensors and can include resistance temperature devices, thermistors, or diode devices such as semiconductor p-n junction diodes. Other types of differential temperature sensing arrangements are contemplated, as well, such as thermocouple configurations with temperature sensing elements 136, 146 representing the measuring points of the thermoelectric effect. In addition, a third temperature sensing element 116 can be disposed in the meter 110 near the interface of the meter 110 where the test sensor 120 is inserted. A microcontroller 118 with an embedded temperature sensor can also be disposed within the meter 110. The third temperature sensor is connected to a processor or a microcontroller of the meter to allow absolute temperature readings to be collected within the meter itself. The meter 110 may also use the same or a different microcontroller or processor for power management, temperature prediction operations, data transfer operation, or to execute other routines associated with the meter 110.

The temperature within the meter 110 is monitored at predetermined intervals or in response to predetermined events. In particular, the temperature sensing element 116 monitors the temperature near the interface with the test sensor 120. When the test sensor 120 is received by the meter 110, a differential temperature reading can be collected from first temperature sensing element 146 and second temperature sensing element 136. As discussed previously, variations from actual ambient temperature in the temperature measurements adversely affect the calculation of the analyte concentration of a fluid sample. Furthermore, the accuracy of the differential temperature reading is increased by approximately one order of magnitude by measuring differential temperatures rather than absolute temperatures. The measured differential readings from sensors 136, 146 are then correlated with temperature to determine the differential temperature between the two sensor elements. The determined differential temperature is used to adjust the meter temperature determined by temperature sensing element 116 to provide an accurate reagent temperature value for the reaction with the analyte in the fluid sample.

FIG. 2 illustrates an example embodiment of a fluid analyte system. In particular, a portable meter 200 includes some or all of the elements discussed for the embodiments described in FIG. 1 and elsewhere herein. As shown in FIG. 2, the meter 200 includes a display 202 visible through a front portion 220, a test-sensor port 204, and a plurality of buttons 206a, 206b. After a user places a sample fluid on a test-sensor that is inserted into the test sensor port 204, the glucose level is determined by the meter 200, which displays the glucose reading on the display 202. The glucose reading is then stored in the meter's memory device.

The meter 200 includes a microprocessor or the like for processing and/or storing data generated during the testing procedure. The meter 200 may also use the same or a different microprocessor for power management or temperature operations, including executing routines to control recharging operations of the meter 200 for battery-operated devices and for implementing temperature prediction algorithms in assessing ambient temperatures.

The test sensor port 204 is adapted to receive and/or hold a test sensor and assist in determining the analyte concentration of a fluid sample. A meter temperature may be monitored for the meter 200 with a meter temperature sensor 260 located at or near the test sensor port 204.

Figure 3:
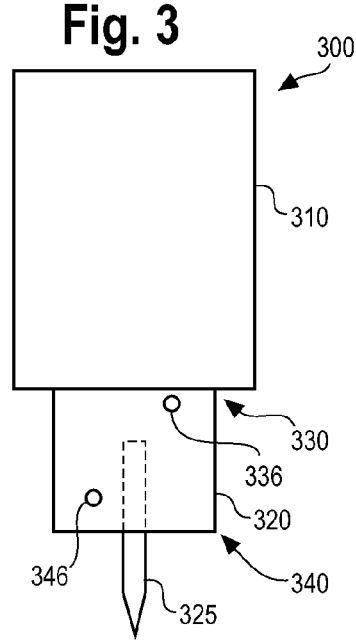
FIG. 3 illustrates a fluid analyte system including a lancing device according to one embodiment.
Figure 4:
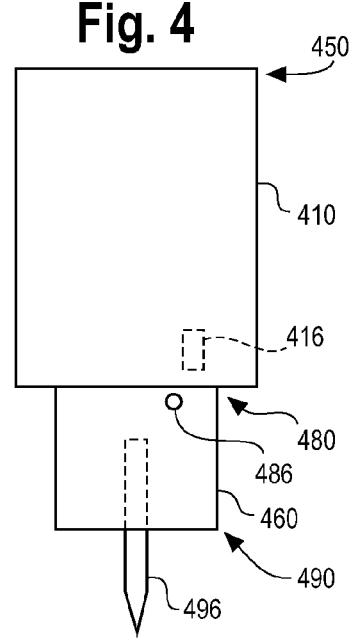
FIG. 4 illustrates a fluid analyte system including a lancing device according to another embodiment.

Turning now to FIGS. 3 and 4, fluid analyte systems 300, 450 are respectively illustrated that include lancing devices 320, 460. Similar to the meter 110 in FIG. 1, meters 310, 410 receive and engage an element that collects a fluid sample. The meter 310, 410 measures the concentration of analyte for the sample collected by the lancing device 320, 460. The meter 310, 410 can include contacts connected to electrodes that detect electrochemical reactions of an electrochemical test sensor within the lancing device 320, 460. The meters 310, 410 may further be configured to perform the operations discussed for the meter 110 in FIG. 1. In certain embodiments, the fluid analyte system 300, 450 may be an integrated system that receives samples, processes analyte concentrations of fluid sample, and/or stores data within a self-contained system including the meter 310, 410 and lancing device 320, 460. In other embodiments, the fluid analyte system 300, 450 may include the lancing device 320, 460 connected to the meter 310, 410 through a wireless connection that transmits the information received at the lancet device.

The lancing device 320, 460 can include a connection end 330, 480 for directly interfacing the lancing device 320, 460 with the respective meter 310, 410. The interface between the lancing device 320, 460, and the meter 310, 410 may be disposed within or at the surface of the meter 310, 410. Lancing device 320, 460 includes a respective lancet 325, 496 for piercing the skin and drawing a sample of bodily fluid, such as a blood sample, into the fluid analyte system. The lancing device 320, 460 can include various arrangements of temperature sensing elements. For example, FIG. 3 illustrates first temperature sensor 346 near fluid-receiving end 340 and second temperature sensor 336 near connection end 330. Sensors 336, 346 may operate together as differential temperature sensors as described above and also below in the context of FIGS. 5-11. In certain embodiments it is contemplated that lancet 325 may operate as a temperature sensor. For example, the lancet 325 can operate similar to a temperature sensor and provide direct readings of ambient temperature without the presence of temperature sensors 336, 346. The use of such as combination lancet and temperature sensor 325 is desirable because the temperature of the lancet can quickly equilibrate with the ambient temperature in the fluid-receiving area or region of the fluid analyte system.

FIG. 4 illustrates the lancing device 460 having a first temperature sensor 486 positioned near the connection end 480 and a combination lancet and temperature sensor 496 positioned at the fluid-receiving end 490 of the lancing device 460. The combination lancets 325, 496 illustrated in the embodiments of FIGS. 3 and 4, respectively, can be configured similar to lancets used in blood glucose monitoring systems, such as the Microlet® 2 lancing system manufactured by Bayer HealthCare LLC. The combination lancets 325, 496 can be made of various materials including silicon carbide, graphite, or noble metals such as platinum or gold.

The lancing device 460 of FIG. 4 can be used as a differential temperature sensor as described herein. For example, the differential temperature can be determined by taking resistance measurements between the first temperature sensor 486 and combination lancet 496. The combination lancet 496 provides a similar temperature measuring function as the temperature sensing element disposed at the fluid-receiving area or region described in FIG. 1. A third temperature sensing element 416 may be present in the meter 410 (e.g., similar to temperature sensor 260 in FIG. 2) for determining the absolute temperature of the meter. The ambient temperature of the meter can then be calculated with a higher degree of accuracy by adding or subtracting the differential temperature, between the temperature sensor 486 and the combination lancet 496, from the absolute temperature determined by the third temperature sensing element.

While the invention has been described with reference to details of the illustrated embodiments, these details are not intended to limit the scope of the invention as defined in the appended claims. For example, although the illustrated embodiments are generally rectangular, it should be noted that the cross-section of the meters and test sensors used herein may be other shapes such as circular, square, hexagonal, octagonal, other polygonal shapes, or oval. The non-electrical components of the illustrated embodiments are typically made of a polymeric material. Non-limiting examples of polymeric materials that may be used in forming the meter include polycarbonate, ABS, nylon, polypropylene, or combinations thereof. It is contemplated that the fluid analyte systems can also be made using non-polymeric materials. The disclosed embodiments and obvious variations thereof are contemplated as falling within the spirit and scope of the claimed invention.

What is claimed is:

1. A test sensor configured to determine a fluid analyte concentration of a fluid sample, the sensor comprising:
    a test sensor body including a first region that has a fluid-receiving area, a second region that is separate from the first region, and a first temperature sensing interface that is disposed at or adjacent to the fluid-receiving area, the fluid-receiving area being configured to receive a fluid sample and allowing the fluid sample to be analyzed to determine a fluid analyte concentration;
    a first conductive trace disposed on the test sensor body, at least a portion of the first conductive trace being disposed in the first region;
    a second conductive trace disposed on the test sensor body; and
    a third conductive trace disposed on the test sensor body, the third conductive trace extending from the first region to the second region, the third conductive trace connected to the first conductive trace at the first temperature sensing interface, the third conductive trace comprised of a different material than the first conductive trace such that a first thermocouple is formed at the first temperature sensing interface, the first thermocouple providing temperature data to assist in determining the fluid analyte concentration,
    wherein the first conductive trace and the second conductive trace are used to determine the fluid analyte concentration of the fluid sample.

2. The test sensor of claim 1, wherein the first conductive trace is a working electrode.

3. The test sensor of claim 1, wherein the third conductive trace is further connected to the second conductive trace at a second temperature sensing interface, the second temperature sensing interface being located in the second region.

4. The test sensor of claim 1, wherein the test sensor body comprises a base and a lid disposed above the base, and the first conductive trace and the third conductive trace are disposed on the base.

5. The test sensor of claim 4, further comprising a counter electrode and working electrode disposed on the lid.

6. The test sensor of claim 1, wherein the test sensor body comprises a base and a lid disposed above the base, and the first conductive trace and the third conductive trace are disposed on the lid.

7. The test sensor of claim 6, further comprising a counter electrode and working electrode disposed on the base.

8. The test sensor of claim 1, wherein the test sensor body comprises a base and a lid, one of the base or the lid including a moveable flap.

9. The test sensor of claim 8, wherein the first temperature sensing interface is located at or adjacent to the moveable flap.

10. The test sensor of claim 1, wherein the first conductive trace and the third conductive trace are electrochemically compatible.

11. The test sensor of claim 10, wherein the first conductive trace comprises a noble metal and the third conductive trace comprises a carbon-based material.

12. A method for making a test sensor configured to determine a fluid analyte concentration of a fluid sample, the method comprising:
    forming a first conductive trace on a test sensor body, the test sensor body including a first region that has a fluid-receiving area, a second region that is separate from the first region, and a first temperature sensing interface that is disposed at or adjacent to the fluid-receiving area, the fluid-receiving area being configured to receive a fluid sample and allowing the fluid sample to be analyzed to determine a fluid analyte concentration, at least a portion of the first conductive trace being disposed in the first region;
    forming a second conductive trace on the test sensor body; and forming a third conductive trace on the test sensor body, the third conductive trace extending from the first region to the second region, the third conductive trace connected to the first conductive trace at the first temperature sensing interface, the third conductive trace comprised of a different material than the first conductive trace such that a first thermocouple is formed at the first temperature sensing interface, the thermocouple providing temperature data to assist in determining the fluid analyte concentration, wherein the first conductive trace and the second conductive trace are used to determine the fluid analyte concentration of the fluid sample.

13. A method for making a test sensor configured to determine a fluid analyte concentration of a fluid sample, the method comprising:

forming a metal layer on a substrate;

attaching the substrate with the metal layer to a test sensor body, the test sensor body including a first region that has a fluid-receiving area, a second region that is separate from the first region, and a first temperature sensing interface that is disposed at or adjacent to the fluid-receiving area, the fluid-receiving area being configured to receive a fluid sample and allowing the fluid sample to be analyzed to determine a fluid analyte concentration;

forming a first conductive trace on the metal layer, at least a portion of the first conductive trace being disposed in the first region;

forming a second conductive trace on the metal layer; and forming a third conductive trace on the metal layer, the third conductive trace extending from the first region to the second region, the third conductive trace connected to the first conductive trace at the first temperature sensing interface, the third conductive trace comprised of a different material than the first conductive trace such that a first thermocouple is formed at the first temperature sensing interface, the thermocouple providing temperature data to assist in determining the fluid analyte concentration.

14. The method of claim 13, wherein the substrate is a plastic material.

15. The method of claim 13, wherein forming a metal layer on the substrate comprises screen printing a metal material on the substrate.

16. The method of claim 13, wherein attaching the substrate to the test sensor body comprises applying the substrate to the test sensor body with the metal layer facing the test sensor body.

17. The method of claim 13, wherein the substrate is with the metal layer is a thin strip.

18. The method of claim 13, wherein forming the first conductive trace, the second conductive trace, and the third conductive trace occurs before the substrate is attached to the test sensor body.

19. The method of claim 18, wherein forming a metal layer on a substrate and forming the first conductive trace, the second conductive trace, and the third conductive trace occurs repeatedly at a standalone production station to form a plurality of strips and each strip is applied to a plurality of test sensor bodies on a separate production line.

* * * * *